(12) United States Patent
McLean et al.

(10) Patent No.: US 8,177,788 B2
(45) Date of Patent: May 15, 2012

(54) IN-LINE MILLING SYSTEM

(75) Inventors: Terry W. McLean, Cordova, TN (US); David C. Kelman, Collierville, TN (US)

(73) Assignee: Smith & Nephew, Inc., Memphis, TN (US)

( * ) Notice: Subject to any disclaimer, the term of this patent is extended or adjusted under 35 U.S.C. 154(b) by 327 days.

(21) Appl. No.: 11/359,794

(22) Filed: Feb. 22, 2006

(65) Prior Publication Data

US 2006/0229626 A1 Oct. 12, 2006

Related U.S. Application Data

(60) Provisional application No. 60/655,171, filed on Feb. 22, 2005, provisional application No. 60/730,184, filed on Oct. 25, 2005.

(51) Int. Cl.
*A61B 17/00* (2006.01)

(52) U.S. Cl. .......................................... 606/80

(58) Field of Classification Search .................. 606/79, 606/130, 80–89, 92–99; 601/2
See application file for complete search history.

(56) References Cited

U.S. PATENT DOCUMENTS

| 100,602 A | 3/1870 | Coes |
|---|---|---|
| 1,076,971 A | 10/1913 | Geiger |
| 1,201,467 A | 10/1916 | Hoglund |
| 2,092,869 A | 9/1937 | Baum |
| 3,412,733 A | 11/1968 | Ross |
| 3,457,922 A | 7/1969 | Ray |
| 3,702,611 A | 11/1972 | Fishbein |
| 4,305,394 A | 12/1981 | Bertuch, Jr. |
| 4,323,080 A | 4/1982 | Melhart |
| 4,393,729 A * | 7/1983 | Wilson .................. 74/473.28 |
| 4,421,112 A | 12/1983 | Mains et al. |
| 4,456,010 A | 6/1984 | Reimels et al. |
| 4,457,307 A | 7/1984 | Stillwell |
| 4,483,554 A | 11/1984 | Ernst |
| 4,524,766 A | 6/1985 | Petersen |
| 4,534,364 A | 8/1985 | Lamoreux |
| 4,565,192 A | 1/1986 | Shapiro |

(Continued)

FOREIGN PATENT DOCUMENTS

DE 042 25 112 C 12/1993

(Continued)

OTHER PUBLICATIONS

International Search Report in related Application No. PCT/US2006/006353.

(Continued)

*Primary Examiner* — Thomas C. Barrett
*Assistant Examiner* — Sameh Boles
(74) *Attorney, Agent, or Firm* — Kilpatrick Townsend & Stockton LLP

(57) ABSTRACT

Embodiments of the present invention provide a milling system and method that provides a precise triangular cut in a patient's proximal femur. The system allows the surgeon to mill in a single direction, that is, the drill is in the same or similar longitudinal place as the handle of the milling system, preventing the surgeon from having to enter the patient's leg at two different angles. The present invention also provides a milling system that can be pre-assembled (e.g., on the back table by a nurse while the surgeon is preparing the site), which enables the milling to take place in one step.

42 Claims, 9 Drawing Sheets

U.S. PATENT DOCUMENTS

| | | |
|---|---|---|
| 4,566,448 A | 1/1986 | Rohr, Jr. |
| 4,567,885 A | 2/1986 | Androphy |
| 4,567,886 A | 2/1986 | Petersen |
| 4,574,794 A | 3/1986 | Cooke et al. |
| 4,583,554 A | 4/1986 | Mittelman et al. |
| 4,671,275 A | 6/1987 | Deyerle |
| 4,703,751 A | 11/1987 | Pohl |
| 4,712,951 A | 12/1987 | Brown |
| 4,718,413 A | 1/1988 | Johnson |
| 4,722,056 A | 1/1988 | Roberts et al. |
| 4,738,256 A | 4/1988 | Freeman et al. |
| 4,759,350 A | 7/1988 | Dunn et al. |
| 4,768,504 A | 9/1988 | Ender |
| 4,777,942 A | 10/1988 | Frey et al. |
| 4,802,468 A | 2/1989 | Powlan |
| 4,803,976 A | 2/1989 | Frigg et al. |
| 4,809,689 A | 3/1989 | Anapliotis |
| 4,815,899 A | 3/1989 | Regan |
| 4,875,475 A | 10/1989 | Comte et al. |
| 4,892,093 A | 1/1990 | Zarnowski et al. |
| 4,913,163 A | 4/1990 | Roger et al. |
| 4,938,762 A | 7/1990 | Wehrli |
| 4,952,213 A | 8/1990 | Bowman et al. |
| 4,964,862 A | 10/1990 | Arms |
| 4,991,579 A | 2/1991 | Allen |
| 5,002,545 A | 3/1991 | Whiteside et al. |
| 5,002,578 A | 3/1991 | Luman |
| 5,016,639 A | 5/1991 | Allen |
| 5,037,423 A | 8/1991 | Kenna |
| 5,037,426 A | 8/1991 | Goble et al. |
| 5,049,149 A | 9/1991 | Schmidt |
| 5,053,039 A | 10/1991 | Hofmann et al. |
| 5,078,719 A | 1/1992 | Schreiber |
| 5,092,869 A | 3/1992 | Waldron |
| 5,094,241 A | 3/1992 | Allen |
| 5,097,839 A | 3/1992 | Allen |
| 5,098,426 A | 3/1992 | Sklar et al. |
| 5,116,338 A | 5/1992 | Poggie et al. |
| 5,119,817 A | 6/1992 | Allen |
| 5,122,144 A | 6/1992 | Bert et al. |
| 5,129,909 A | 7/1992 | Sutherland |
| 5,147,408 A | 9/1992 | Noble |
| 5,190,547 A | 3/1993 | Barber, Jr. et al. |
| 5,211,164 A | 5/1993 | Allen |
| 5,213,312 A | 5/1993 | MacDonald |
| 5,217,499 A | 6/1993 | Shelley |
| 5,230,338 A | 7/1993 | Allen et al. |
| 5,246,444 A | 9/1993 | Schreiber |
| 5,254,119 A | 10/1993 | Schreiber |
| 5,263,972 A | 11/1993 | Evans et al. |
| 5,289,826 A | 3/1994 | Kovacevic |
| 5,305,203 A | 4/1994 | Raab |
| 5,342,363 A * | 8/1994 | Richelsoph ............ 606/79 |
| 5,342,366 A | 8/1994 | Whiteside et al. |
| 5,342,969 A * | 8/1994 | Ford et al. ............ 549/274 |
| 5,360,016 A | 11/1994 | Kovacevic |
| 5,364,401 A | 11/1994 | Ferrante et al. |
| 5,364,402 A | 11/1994 | Mumme et al. |
| 5,365,996 A | 11/1994 | Crook |
| 5,375,588 A | 12/1994 | Yoon |
| 5,379,133 A | 1/1995 | Kirk |
| 5,383,454 A | 1/1995 | Bucholz |
| 5,387,218 A * | 2/1995 | Meswania ............ 606/80 |
| 5,389,101 A | 2/1995 | Heilbrun et al. |
| 5,395,376 A | 3/1995 | Caspari et al. |
| 5,397,329 A | 3/1995 | Allen |
| 5,403,320 A | 4/1995 | Luman |
| 5,423,828 A | 6/1995 | Benson |
| 5,425,355 A | 6/1995 | Kulick |
| 5,445,166 A | 8/1995 | Taylor |
| 5,445,642 A | 8/1995 | McNulty et al. |
| 5,449,360 A | 9/1995 | Schreiber |
| 5,452,407 A | 9/1995 | Crook |
| 5,462,548 A | 10/1995 | Pappas et al. |
| 5,462,549 A | 10/1995 | Glock |
| 5,468,244 A | 11/1995 | Attfield et al. |
| 5,470,354 A | 11/1995 | Hershberger et al. |
| 5,474,559 A | 12/1995 | Bertin et al. |
| 5,484,437 A | 1/1996 | Michelson |
| 5,486,178 A | 1/1996 | Hodge |
| 5,490,854 A | 2/1996 | Fisher et al. |
| 5,491,510 A | 2/1996 | Gove |
| 5,507,824 A | 4/1996 | Lennox |
| 5,514,139 A | 5/1996 | Goldstein et al. |
| 5,517,990 A | 5/1996 | Kalfas et al. |
| 5,527,316 A | 6/1996 | Williamson |
| 5,540,691 A | 7/1996 | Elmstrom et al. |
| 5,540,694 A | 7/1996 | DeCarlo, Jr. |
| 5,540,695 A | 7/1996 | Levy |
| 5,540,696 A | 7/1996 | Booth, Jr. et al. |
| 5,569,260 A | 10/1996 | Petersen |
| 5,597,379 A | 1/1997 | Haines et al. |
| 5,598,269 A | 1/1997 | Kitaevich et al. |
| 5,603,318 A | 2/1997 | Heilbrun et al. |
| 5,613,969 A | 3/1997 | Jenkins, Jr. |
| 5,643,268 A | 7/1997 | Vilsmeier et al. |
| 5,643,272 A | 7/1997 | Haines et al. |
| 5,658,290 A | 8/1997 | Lechot |
| 5,669,914 A | 9/1997 | Eckhoff |
| 5,676,668 A | 10/1997 | McCue et al. |
| 5,681,316 A | 10/1997 | DeOrio et al. |
| 5,682,886 A | 11/1997 | Delp et al. |
| 5,683,397 A | 11/1997 | Vendrely et al. |
| 5,688,279 A | 11/1997 | McNulty et al. |
| 5,693,056 A | 12/1997 | Carls et al. |
| 5,695,501 A | 12/1997 | Carol et al. |
| 5,702,406 A | 12/1997 | Vilsmeier et al. |
| 5,704,941 A | 1/1998 | Jacober et al. |
| 5,707,370 A | 1/1998 | Berki et al. |
| 5,709,689 A | 1/1998 | Ferrante et al. |
| 5,715,836 A | 2/1998 | Kliegis et al. |
| 5,716,361 A | 2/1998 | Masini |
| 5,720,752 A | 2/1998 | Elliott et al. |
| 5,722,978 A | 3/1998 | Jenkins, Jr. |
| 5,733,292 A | 3/1998 | Gustilo et al. |
| 5,735,904 A | 4/1998 | Pappas |
| 5,743,915 A | 4/1998 | Bertin et al. |
| 5,748,767 A | 5/1998 | Raab |
| 5,755,725 A | 5/1998 | Druais |
| 5,755,803 A | 5/1998 | Haines et al. |
| 5,769,861 A | 6/1998 | Vilsmeier |
| 5,772,593 A | 6/1998 | Hakamata |
| 5,772,594 A | 6/1998 | Barrick |
| 5,776,064 A | 7/1998 | Kalfas et al. |
| 5,782,842 A | 7/1998 | Kloess et al. |
| 5,792,147 A | 8/1998 | Evans et al. |
| 5,797,924 A | 8/1998 | Schulte et al. |
| 5,799,055 A | 8/1998 | Peshkin et al. |
| 5,800,352 A | 9/1998 | Ferre et al. |
| 5,800,438 A | 9/1998 | Tuke et al. |
| 5,807,252 A | 9/1998 | Hassfeld et al. |
| 5,810,827 A | 9/1998 | Haines et al. |
| 5,810,841 A | 9/1998 | McNeirney et al. |
| 5,817,097 A | 10/1998 | Howard et al. |
| 5,830,214 A | 11/1998 | Flom et al. |
| 5,836,954 A | 11/1998 | Heilbrun et al. |
| 5,848,967 A | 12/1998 | Cosman |
| 5,850,836 A | 12/1998 | Steiger et al. |
| 5,860,981 A | 1/1999 | Bertin et al. |
| 5,865,809 A | 2/1999 | Moenning et al. |
| 5,871,018 A | 2/1999 | Delp et al. |
| 5,871,445 A | 2/1999 | Bucholz |
| 5,879,352 A | 3/1999 | Filoso et al. |
| 5,879,354 A | 3/1999 | Haines et al. |
| 5,880,976 A | 3/1999 | DiGioia, III et al. |
| 5,885,296 A | 3/1999 | Masini |
| 5,885,297 A | 3/1999 | Matsen, III |
| 5,897,559 A | 4/1999 | Masini |
| 5,916,221 A | 6/1999 | Hodorek et al. |
| 5,920,395 A | 7/1999 | Schulz |
| 5,921,992 A | 7/1999 | Costales et al. |
| 5,925,049 A | 7/1999 | Gustilo et al. |
| 5,935,128 A | 8/1999 | Carter et al. |
| 5,938,665 A | 8/1999 | Martin |
| 5,944,722 A | 8/1999 | Masini |
| 5,947,971 A | 9/1999 | Kuslich et al. |
| 5,947,973 A | 9/1999 | Masini |

| | | | |
|---|---|---|---|
| 5,951,561 A | 9/1999 | Pepper et al. | |
| 5,957,926 A | 9/1999 | Masini | |
| 5,961,523 A | 10/1999 | Masini | |
| 5,971,989 A | 10/1999 | Masini | |
| 5,980,526 A | 11/1999 | Johnson et al. | |
| 5,980,535 A | 11/1999 | Barnett et al. | |
| 5,999,837 A | 12/1999 | Messner et al. | |
| 6,001,106 A | 12/1999 | Ryan et al. | |
| 6,002,859 A | 12/1999 | DiGioia, III et al. | |
| 6,006,126 A | 12/1999 | Cosman | |
| 6,006,127 A | 12/1999 | Van Der Brug et al. | |
| 6,007,537 A | 12/1999 | Burkinshaw et al. | |
| 6,010,506 A | 1/2000 | Gosney et al. | |
| 6,011,987 A | 1/2000 | Barnett | |
| 6,016,606 A | 1/2000 | Oliver et al. | |
| 6,021,342 A | 2/2000 | Brabrand | |
| 6,021,343 A | 2/2000 | Foley et al. | |
| 6,022,377 A | 2/2000 | Nuelle et al. | |
| 6,026,315 A | 2/2000 | Lenz et al. | |
| 6,030,391 A | 2/2000 | Brainard et al. | |
| 6,033,410 A | 3/2000 | McLean et al. | |
| 6,041,249 A | 3/2000 | Regn | |
| 6,044,291 A | 3/2000 | Rockseisen | |
| 6,045,556 A | 4/2000 | Cohen | |
| 6,050,724 A | 4/2000 | Schmitz et al. | |
| 6,053,922 A | 4/2000 | Krause et al. | |
| 6,056,756 A | 5/2000 | Eng et al. | |
| 6,068,633 A | 5/2000 | Masini | |
| 6,069,932 A | 5/2000 | Peshkin et al. | |
| 6,073,044 A | 6/2000 | Fitzpatrick et al. | |
| 6,077,269 A | 6/2000 | Masini | |
| 6,081,336 A | 6/2000 | Messner et al. | |
| 6,083,163 A | 7/2000 | Wegner et al. | |
| 6,096,048 A | 8/2000 | Howard et al. | |
| 6,102,916 A | 8/2000 | Masini | |
| 6,132,433 A | 10/2000 | Whelan | |
| 6,143,390 A | 11/2000 | Takamiya et al. | |
| 6,144,875 A | 11/2000 | Schweikard et al. | |
| 6,146,390 A | 11/2000 | Heilbrun et al. | |
| 6,148,280 A | 11/2000 | Kramer | |
| 6,161,033 A | 12/2000 | Kuhn | |
| 6,162,190 A | 12/2000 | Kramer | |
| 6,165,181 A | 12/2000 | Heilbrun et al. | |
| 6,167,145 A | 12/2000 | Foley et al. | |
| 6,167,292 A | 12/2000 | Badano et al. | |
| 6,167,295 A | 12/2000 | Cosman | |
| 6,167,296 A | 12/2000 | Shahidi | |
| 6,168,627 B1 | 1/2001 | Huebner | |
| 6,174,335 B1 | 1/2001 | Varieur | |
| 6,185,315 B1 | 2/2001 | Schmucker et al. | |
| 6,187,010 B1 | 2/2001 | Masini | |
| 6,190,320 B1 | 2/2001 | Lelong | |
| 6,190,395 B1 | 2/2001 | Williams | |
| 6,195,168 B1 | 2/2001 | De Lega et al. | |
| 6,197,064 B1 | 3/2001 | Haines et al. | |
| 6,198,794 B1 | 3/2001 | Peshkin et al. | |
| 6,200,316 B1 | 3/2001 | Zwirkoski et al. | |
| 6,205,411 B1 | 3/2001 | DiGioia, III et al. | |
| 6,211,976 B1 | 4/2001 | Popovich et al. | |
| 6,214,011 B1 | 4/2001 | Masini | |
| 6,216,029 B1 | 4/2001 | Paltieli | |
| 6,223,067 B1 | 4/2001 | Vilsmeier et al. | |
| 6,226,548 B1 | 5/2001 | Foley et al. | |
| 6,228,090 B1 | 5/2001 | Waddell | |
| 6,228,092 B1 | 5/2001 | Mikhail | |
| 6,235,038 B1 | 5/2001 | Hunter et al. | |
| 6,236,875 B1 | 5/2001 | Bucholz et al. | |
| 6,241,735 B1 | 6/2001 | Marmulla | |
| 6,249,581 B1 | 6/2001 | Kok | |
| 6,258,095 B1 | 7/2001 | Lombardo et al. | |
| 6,258,096 B1 | 7/2001 | Seki | |
| 6,264,647 B1 | 7/2001 | Lechot | |
| 6,283,971 B1 | 9/2001 | Temeles | |
| 6,285,902 B1 | 9/2001 | Kienzle, III et al. | |
| 6,295,513 B1 | 9/2001 | Thackston | |
| 6,317,616 B1 | 11/2001 | Glossop | |
| 6,319,256 B1 | 11/2001 | Spotorno | |
| 6,332,891 B1 | 12/2001 | Himes | |
| 6,333,971 B2 | 12/2001 | McCrory et al. | |
| 6,344,853 B1 | 2/2002 | Knight | |
| 6,347,240 B1 | 2/2002 | Foley et al. | |
| 6,351,659 B1 | 2/2002 | Vilsmeier | |
| 6,351,661 B1 | 2/2002 | Cosman | |
| 6,377,839 B1 | 4/2002 | Kalfas et al. | |
| 6,383,188 B2 | 5/2002 | Kuslich et al. | |
| 6,385,475 B1 | 5/2002 | Cinquin et al. | |
| 6,405,072 B1 | 6/2002 | Cosman | |
| 6,413,261 B1 | 7/2002 | Grundei | |
| 6,434,507 B1 | 8/2002 | Clayton et al. | |
| 6,440,140 B2 | 8/2002 | Bullivant et al. | |
| 6,443,956 B1 | 9/2002 | Ray | |
| 6,451,059 B1 | 9/2002 | Janas et al. | |
| 6,458,135 B1 | 10/2002 | Harwin et al. | |
| 6,463,351 B1 | 10/2002 | Clynch | |
| 6,468,202 B1 | 10/2002 | Irion et al. | |
| 6,477,400 B1 | 11/2002 | Barrick | |
| 6,478,799 B1 | 11/2002 | Williamson | |
| 6,484,049 B1 | 11/2002 | Seeley et al. | |
| 6,490,467 B1 | 12/2002 | Bucholz et al. | |
| 6,491,429 B1 | 12/2002 | Suhm | |
| 6,491,702 B2 | 12/2002 | Heilbrun et al. | |
| 6,494,913 B1 * | 12/2002 | Huebner | 623/19.11 |
| 6,503,249 B1 | 1/2003 | Krause | |
| 6,503,254 B1 | 1/2003 | Masini | |
| 6,527,443 B1 | 3/2003 | Vilsmeier et al. | |
| 6,540,739 B2 | 4/2003 | Lechot | |
| 6,546,279 B1 | 4/2003 | Bova et al. | |
| 6,551,319 B2 | 4/2003 | Lieberman | |
| 6,551,324 B2 | 4/2003 | Muller | |
| 6,551,325 B2 | 4/2003 | Neubauer et al. | |
| 6,554,837 B1 | 4/2003 | Hauri et al. | |
| 6,558,391 B2 | 5/2003 | Axelson, Jr. et al. | |
| 6,558,421 B1 | 5/2003 | Fell et al. | |
| 6,567,687 B2 | 5/2003 | Front et al. | |
| 6,574,493 B2 | 6/2003 | Rasche et al. | |
| 6,595,997 B2 | 7/2003 | Axelson, Jr. et al. | |
| 6,602,259 B1 | 8/2003 | Masini | |
| 6,620,168 B1 | 9/2003 | Lombardo et al. | |
| 6,620,268 B2 | 9/2003 | Cho et al. | |
| 6,640,127 B1 | 10/2003 | Kosaka et al. | |
| 6,652,142 B2 | 11/2003 | Launay et al. | |
| 6,662,036 B2 | 12/2003 | Cosman | |
| 6,673,077 B1 | 1/2004 | Katz | |
| 6,675,040 B1 | 1/2004 | Cosman | |
| 6,685,711 B2 | 2/2004 | Axelson, Jr. et al. | |
| 6,690,964 B2 | 2/2004 | Bieger et al. | |
| 6,692,447 B1 | 2/2004 | Picard | |
| 6,695,848 B2 | 2/2004 | Haines | |
| 6,702,821 B2 | 3/2004 | Bonutti | |
| 6,711,431 B2 | 3/2004 | Sarin et al. | |
| 6,712,823 B2 | 3/2004 | Grusin et al. | |
| 6,712,824 B2 | 3/2004 | Millard et al. | |
| 6,716,249 B2 | 4/2004 | Hyde | |
| 6,718,194 B2 | 4/2004 | Kienzle | |
| 6,725,080 B2 | 4/2004 | Melkent et al. | |
| 6,725,082 B2 | 4/2004 | Sati et al. | |
| 6,728,599 B2 | 4/2004 | Wang | |
| 6,729,211 B1 * | 5/2004 | Snow | 81/177.75 |
| 6,772,026 B2 | 8/2004 | Bradbury et al. | |
| 6,780,190 B2 | 8/2004 | Maroney | |
| 6,785,593 B2 | 8/2004 | Wang | |
| 6,799,088 B2 | 9/2004 | Wang | |
| 6,814,490 B1 | 11/2004 | Suhm et al. | |
| 6,827,723 B2 | 12/2004 | Carson | |
| 6,836,703 B2 | 12/2004 | Wang | |
| 6,871,117 B2 | 3/2005 | Wang | |
| 6,882,982 B2 | 4/2005 | McMenimem | |
| 6,892,112 B2 | 5/2005 | Wang et al. | |
| 6,905,514 B2 | 6/2005 | Carignan et al. | |
| 6,923,817 B2 | 8/2005 | Carson | |
| 6,947,786 B2 | 9/2005 | Simon et al. | |
| 6,993,374 B2 | 1/2006 | Sasso | |
| 7,001,346 B2 | 2/2006 | White | |
| 7,035,702 B2 | 4/2006 | Jelonek et al. | |
| 7,237,556 B2 | 7/2007 | Smothers | |
| 7,241,298 B2 | 7/2007 | Nemec et al. | |
| 2001/0001120 A1 | 5/2001 | Masini | |
| 2001/0014772 A1 | 8/2001 | Lampotang et al. | |

| | | |
|---|---|---|
| 2001/0016745 A1 | 8/2001 | Bullivant et al. |
| 2001/0034530 A1 | 10/2001 | Malackowski et al. |
| 2001/0036245 A1 | 11/2001 | Kienzle, III et al. |
| 2001/0039421 A1 | 11/2001 | Heilbrun et al. |
| 2002/0002330 A1 | 1/2002 | Vilsmeier |
| 2002/0002365 A1 | 1/2002 | Lechot |
| 2002/0007294 A1 | 1/2002 | Bradbury et al. |
| 2002/0011594 A1 | 1/2002 | DeSouza |
| 2002/0016540 A1 | 2/2002 | Mikus et al. |
| 2002/0018981 A1 | 2/2002 | Andersson et al. |
| 2002/0029041 A1 | 3/2002 | Hover et al. |
| 2002/0032451 A1 | 3/2002 | Tierney et al. |
| 2002/0038085 A1 | 3/2002 | Immerz |
| 2002/0052606 A1 | 5/2002 | Bonutti |
| 2002/0065461 A1 | 5/2002 | Cosman |
| 2002/0068942 A1 | 6/2002 | Neubauer et al. |
| 2002/0072748 A1 | 6/2002 | Robioneck |
| 2002/0072821 A1 | 6/2002 | Baker |
| 2002/0077533 A1 | 6/2002 | Bieger et al. |
| 2002/0077540 A1 | 6/2002 | Kienzle, III |
| 2002/0085681 A1 | 7/2002 | Jensen |
| 2002/0087101 A1 | 7/2002 | Barrick et al. |
| 2002/0095081 A1 | 7/2002 | Vilsmeier |
| 2002/0102214 A1 | 8/2002 | Briley-Saebo et al. |
| 2002/0107518 A1 | 8/2002 | Neubauer et al. |
| 2002/0115934 A1 | 8/2002 | Tuke |
| 2002/0133161 A1 | 9/2002 | Axelson, Jr. et al. |
| 2002/0133175 A1* | 9/2002 | Carson ............ 606/130 |
| 2002/0147455 A1 | 10/2002 | Carson |
| 2002/0151894 A1 | 10/2002 | Melkent et al. |
| 2002/0151898 A1 | 10/2002 | Sohngen et al. |
| 2002/0156371 A1 | 10/2002 | Hedlund et al. |
| 2002/0156479 A1 | 10/2002 | Schulzki et al. |
| 2002/0188194 A1 | 12/2002 | Cosman |
| 2002/0193800 A1 | 12/2002 | Kienzle, III et al. |
| 2002/0198448 A1 | 12/2002 | Zuk et al. |
| 2002/0198451 A1 | 12/2002 | Carson |
| 2002/0198531 A1 | 12/2002 | Millard et al. |
| 2003/0006107 A1 | 1/2003 | Thompson |
| 2003/0018338 A1 | 1/2003 | Axelson, Jr. et al. |
| 2003/0045883 A1 | 3/2003 | Chow et al. |
| 2003/0050643 A1 | 3/2003 | Taft |
| 2003/0069591 A1 | 4/2003 | Carson |
| 2003/0073901 A1 | 4/2003 | Simon et al. |
| 2003/0153829 A1 | 8/2003 | Sarin et al. |
| 2003/0153859 A1 | 8/2003 | Hinshon |
| 2003/0153978 A1 | 8/2003 | Whiteside |
| 2003/0164172 A1 | 9/2003 | Chumas et al. |
| 2003/0181918 A1 | 9/2003 | Smothers et al. |
| 2003/0187351 A1 | 10/2003 | Franck et al. |
| 2003/0187452 A1 | 10/2003 | Smith et al. |
| 2003/0192557 A1 | 10/2003 | Krag et al. |
| 2003/0225329 A1 | 12/2003 | Rossner et al. |
| 2004/0019382 A1 | 1/2004 | Amirouche et al. |
| 2004/0030237 A1 | 2/2004 | Lee et al. |
| 2004/0030245 A1 | 2/2004 | Noble et al. |
| 2004/0054489 A1 | 3/2004 | Moctezuma De La Barrera |
| 2004/0073279 A1 | 4/2004 | Malackowski et al. |
| 2004/0087852 A1 | 5/2004 | Chen et al. |
| 2004/0097952 A1 | 5/2004 | Sarin et al. |
| 2004/0152970 A1 | 8/2004 | Hunter et al. |
| 2004/0153081 A1 | 8/2004 | Tulkis |
| 2004/0153083 A1 | 8/2004 | Nemec et al. |
| 2004/0167391 A1 | 8/2004 | Solar et al. |
| 2004/0171924 A1 | 9/2004 | Mire et al. |
| 2004/0243481 A1 | 12/2004 | Bradbury et al. |
| 2004/0254586 A1 | 12/2004 | Sarin |
| 2004/0260290 A1 | 12/2004 | Zander et al. |
| 2005/0021037 A1 | 1/2005 | McCombs et al. |
| 2005/0021043 A1 | 1/2005 | Jansen |
| 2005/0075632 A1 | 4/2005 | Russell et al. |
| 2005/0085715 A1 | 4/2005 | Dukesherer et al. |
| 2005/0085822 A1 | 4/2005 | Thornberry et al. |
| 2005/0101966 A1 | 5/2005 | Lavallee |
| 2005/0109855 A1 | 5/2005 | McCombs |
| 2005/0113658 A1 | 5/2005 | Jacobson et al. |
| 2005/0113659 A1 | 5/2005 | Pothier |
| 2005/0113846 A1 | 5/2005 | Carson |
| 2005/0119639 A1 | 6/2005 | McCombs |
| 2005/0119777 A1 | 6/2005 | Arbogast et al. |
| 2005/0124988 A1 | 6/2005 | Terrill-Grisoni et al. |
| 2005/0148843 A1 | 7/2005 | Roose |
| 2005/0149003 A1 | 7/2005 | Tierney et al. |
| 2005/0149041 A1 | 7/2005 | McGinley |
| 2005/0154331 A1* | 7/2005 | Christie et al. ............ 601/2 |
| 2005/0159759 A1 | 7/2005 | Harbaugh et al. |
| 2005/0177172 A1 | 8/2005 | Acker |
| 2005/0197569 A1 | 9/2005 | McCombs |
| 2005/0197814 A1 | 9/2005 | Aram et al. |
| 2005/0203384 A1 | 9/2005 | Sati et al. |
| 2005/0209726 A1 | 9/2005 | Voit et al. |
| 2005/0216305 A1 | 9/2005 | Funderud |
| 2005/0228266 A1 | 10/2005 | McCombs |
| 2005/0228404 A1 | 10/2005 | Vandevelde |
| 2005/0234332 A1 | 10/2005 | Murphy |
| 2005/0234465 A1 | 10/2005 | McCombs et al. |
| 2005/0234466 A1 | 10/2005 | Stallings |
| 2005/0234468 A1 | 10/2005 | Carson |
| 2005/0245808 A1 | 11/2005 | Carson |
| 2005/0279368 A1 | 12/2005 | McCombs |
| 2005/0288676 A1 | 12/2005 | Schnieders |
| 2006/0015120 A1 | 1/2006 | Richard et al. |
| 2006/0149285 A1* | 7/2006 | Burgi et al. ............ 606/99 |
| 2006/0161051 A1 | 7/2006 | Terrill-Grisoni et al. |
| 2006/0190011 A1 | 8/2006 | Ries |
| 2006/0200025 A1 | 9/2006 | Elliott |
| 2007/0118055 A1 | 5/2007 | McCombs |
| 2007/0123912 A1 | 5/2007 | Carson |
| 2007/0169782 A1 | 7/2007 | Castleman |

FOREIGN PATENT DOCUMENTS

| | | |
|---|---|---|
| DE | 296 00 990 U1 | 4/1996 |
| DE | 196 29 011 A1 | 1/1998 |
| DE | 197 09 960 A1 | 9/1998 |
| DE | 299 06 438 U1 | 9/1999 |
| DE | 296 23 941 U1 | 11/2000 |
| DE | 200 21 494 U1 | 3/2001 |
| DE | 201 03 416 U1 | 7/2001 |
| DE | 100 12 042 C1 | 8/2001 |
| DE | 100 31 887 A1 | 1/2002 |
| DE | 102 07 035 | 2/2002 |
| DE | 100 45 381 A1 | 4/2002 |
| DE | 202 13 243 U1 | 10/2002 |
| DE | 203 09 399 U1 | 8/2003 |
| EP | 0 337 901 A1 | 10/1989 |
| EP | 0 340 176 A2 | 11/1989 |
| EP | 0 216 794 B1 | 12/1989 |
| EP | 0 366 488 B1 | 5/1990 |
| EP | 0 376 657 B1 | 7/1990 |
| EP | 0 380 451 A2 | 8/1990 |
| EP | 0 415 837 A2 | 3/1991 |
| EP | 0 466 659 A2 | 1/1992 |
| EP | 0 359 097 B1 | 8/1992 |
| EP | 0 538 152 A1 | 4/1993 |
| EP | 0 538 153 B1 | 4/1993 |
| EP | 0 555 003 B1 | 8/1993 |
| EP | 0 428 303 B1 | 7/1995 |
| EP | 0 676 178 A1 | 10/1995 |
| EP | 0 720 834 A2 | 7/1996 |
| EP | 0 619 097 B1 | 6/1999 |
| EP | 0 1 149 562 A2 | 10/2001 |
| EP | 1 033 108 A1 | 2/2002 |
| EP | 1 190 676 A1 | 3/2002 |
| EP | 1 226 788 A1 | 7/2002 |
| EP | 0 782 842 B1 | 9/2002 |
| EP | 1 236 450 A1 | 9/2002 |
| EP | 1 249 207 A2 | 10/2002 |
| EP | 1 348 384 A | 10/2003 |
| EP | 1 384 456 A2 | 1/2004 |
| EP | 0 406 203 A2 | 4/2004 |
| EP | 0 406 203 A3 | 4/2004 |
| EP | 1 405 603 A2 | 4/2004 |
| EP | 1 435 223 A1 | 7/2004 |
| EP | 0 327 509 A1 | 8/2004 |
| EP | 0 327 509 B1 | 8/2004 |
| EP | 1 442 715 A2 | 8/2004 |
| EP | 1 459 686 A2 | 9/2004 |
| EP | 1 532 946 A2 | 5/2005 |

| | | | |
|---|---|---|---|
| EP | 1 563 795 A1 | 8/2005 |
| FR | 2 828 397 A | 2/2003 |
| GB | 2 224 937 | 5/1990 |
| GB | 2 397 769 A | 8/2004 |
| JP | 2002-304439 | 10/2002 |
| WO | WO 86/05384 | 9/1986 |
| WO | WO 89/09570 | 10/1989 |
| WO | WO 94/17733 | 8/1994 |
| WO | WO 95/15714 | 6/1995 |
| WO | WO 96/35387 | 11/1996 |
| WO | WO 97/16129 | 5/1997 |
| WO | WO 97/23172 | 7/1997 |
| WO | WO 97/29683 | 8/1997 |
| WO | WO 98/29032 | 7/1998 |
| WO | WO 98/46169 | 10/1998 |
| WO | WO 99/15097 | 4/1999 |
| WO | WO 99/27860 | 6/1999 |
| WO | WO 99/60939 | 12/1999 |
| WO | WO 99/65380 | 12/1999 |
| WO | WO 00/00093 | 1/2000 |
| WO | WO 00/21442 | 4/2000 |
| WO | WO 00/47103 | 8/2000 |
| WO | WO 00/64367 | 11/2000 |
| WO | WO 01/01845 A2 | 1/2001 |
| WO | WO 01/19271 A2 | 3/2001 |
| WO | WO 01/34050 | 5/2001 |
| WO | WO 01/64124 A1 | 9/2001 |
| WO | WO 01/67979 A1 | 9/2001 |
| WO | WO 01/91647 A1 | 12/2001 |
| WO | WO 01/93770 A1 | 12/2001 |
| WO | WO 02/24096 A1 | 3/2002 |
| WO | WO 02/41794 A1 | 5/2002 |
| WO | WO 02/063236 A2 | 8/2002 |
| WO | WO 02/063236 A3 | 8/2002 |
| WO | WO 02/064042 A1 | 8/2002 |
| WO | WO 02/067783 A3 | 9/2002 |
| WO | WO 02/067784 A2 | 9/2002 |
| WO | WO 02/067800 A2 | 9/2002 |
| WO | WO 02/080824 A1 | 10/2002 |
| WO | WO 03/006107 A1 | 1/2003 |
| WO | WO 03/015642 A1 | 2/2003 |
| WO | WO 03/030787 | 4/2003 |
| WO | WO 03/030787 A1 | 4/2003 |
| WO | WO 03/034213 A2 | 4/2003 |
| WO | WO 03/034933 A1 | 5/2003 |
| WO | WO 03/037192 A1 | 5/2003 |
| WO | WO 03/039377 A1 | 5/2003 |
| WO | WO 03/041566 A2 | 5/2003 |
| WO | WO 03/065931 | 8/2003 |
| WO | WO 03/065949 A2 | 8/2003 |
| WO | WO 03/068090 A1 | 8/2003 |
| WO | WO 03/071969 A1 | 9/2003 |
| WO | WO 03/075740 A2 | 9/2003 |
| WO | WO 03/079940 A2 | 10/2003 |
| WO | WO 03/096870 A2 | 11/2003 |
| WO | WO 2004/001569 A2 | 12/2003 |
| WO | WO 2004/017842 A2 | 3/2004 |
| WO | WO 2004/019792 A1 | 3/2004 |
| WO | WO 2004/029908 A1 | 4/2004 |
| WO | WO 2004/030556 A1 | 4/2004 |
| WO | WO 2004/030559 A1 | 4/2004 |
| WO | WO 2004/046754 A2 | 6/2004 |
| WO | WO 2004/069036 A2 | 8/2004 |
| WO | WO 2004/070580 A2 | 8/2004 |
| WO | WO 2004/084740 A1 | 10/2004 |
| WO | WO 2005/009303 A1 | 2/2005 |
| WO | WO 2005/039430 A2 | 5/2005 |
| WO | WO 2005/041802 A1 | 5/2005 |
| WO | WO 2005/044126 A1 | 5/2005 |
| WO | WO 2005/048851 A1 | 6/2005 |
| WO | WO 2005/053559 A1 | 6/2005 |
| WO | WO 2005/057439 A1 | 6/2005 |
| WO | WO 2005/070312 A1 | 8/2005 |
| WO | WO 2005/070319 A1 | 8/2005 |
| WO | WO 2005/072629 A1 | 8/2005 |
| WO | WO 2005/096982 A1 | 10/2005 |
| WO | WO 2005/104977 A1 | 11/2005 |
| WO | WO 2005/104978 A1 | 11/2005 |
| WO | WO 2006/044367 A1 | 4/2006 |
| WO | WO 2006/060631 A1 | 6/2006 |
| WO | WO 2006/078236 A1 | 7/2006 |
| WO | WO 2008/021494 | 2/2008 |

OTHER PUBLICATIONS

DePuy, a Johnson & Johnson Company, Brochure entitled 'S-ROM Modular Hip System Minimally Invasive Calcar Miller Surgical Technique,' 12 pages (2004).

AO Development Institute: "MEPUC Motorized Exact Positioning Unit for C-arm," 1 page (undated); http://www/ao-asif.ch/development/adi/examples/mepuc.shtml.

Barnes, et al.: "Unicompartmental Knee Arthroplasty," *Bombay Hospital Journal*, Issue Special, pp. 1-5; www.bhj.org/journal/1996/3803_july/special_486.htm.

Bonutti, et al.: "Minimal Incision Total Knee Arthroplasty Using the Suspended Leg Technique," *Orthopedics*, (Sep. 2003), 6 pages; http://www.orthobluejournal.corn/0903/9tips.asp.

BrainLAB: "Ortho—Your Partner for the Future," Brochure, pp. 1-28 (2002).

Corinth Surgeon Performs Revolutionary Hip Replacement, Mississippi Medical News, pp. 1-2 (Nov. 17, 2005) http://host1.bondware.com/~mississippi/news.php?viewStory=347.

Croitoru, et al: "Fixation-Based Surgery: A New Technique for Distal Radius Osteotomy," *Computer Aided Surgery* 160-169, vol. 6 (2001).

Dario, et al., 'Smart Surgical Tools and Augmenting Devices,' IEEE Trans. Rob. Autom., 19(5):782-792 (2003).

Delp, et al.: "Computer-Assisted Knee Replacement," *Clinical Orthopaedics and Related Research*, 354:49-56 (1998).

Deluzio, et al.: "Static alignment and the adduction moment in unicompartmental arthroplasty patients"; presented at NACOB 98: North American Congress on Biomechanics, University of Waterloo, Ontario, Canada, Aug. 14-18, 1998.

DiGioia, III, et al.: "Computer Assisted Orthopedic Surgery," *Clinical Orthopaedics and Related Research*, Sep. 1998, vol. 354, pp. 8-16.

Ellis, et al.: "A Surgical Planning and Guidance System for High Tibial Osteotomy," *Journal of Computer-Assisted Surgery*, 4(5):264-274 (1999).

Fernandez-Lozano, et al., 'Human-machine interface evaluation in a computer assisted surgical system,' Proc. IEEE Int. Conf. Rob. Autom., 2004:231-236 (2004).

Foley, et al.: "Percutaneous pedicle screw fixation of the lumbar spine," *Neurosurg. Focus*, vol. 10(4), pp. 1-8 (2001).

Glossop: http://www.traxtal.com/papers/cua/node1.html; 8 pages (Apr. 21, 1997).

Hafez, et al., 'Computer-Assisted Total Knee Arthroplasty Using Patient-Specific Templating,' *Clinical Orthopaedics and Related Research*, No. 444, pp. 184-192 (2006).

iON™ Smith & Nephew Orthopaedics brochure: "You'll Never Look At Your Patients the Same Way Again"; 10 pages (Jan. 2001).

Iyun, et al.: "Planning and Performing the Ilizarov Method with the Taylor Spatial Frame," 2nd Annual Meeting of International Society for Computer Assisted Orthopaedic Surgery, Jun. 21, 2002, pp. 145-147 (abstract).

Kanade, et al.: "Image-Based Computer Assisted Orthopedic Surgery System," Bonecraft, Inc.;12 pages, Apr. 30, 2001.

Kiefer, et al.: "Computer Aided Knee Arthroplasty Versus Conventional Technique—First Results"; First Annual Meeting of the International Society for Computer Assisted Orthopedic Surgery, Davos, Switzerland, Feb. 8-10, 2001.

Kunz, et al.: "Development and Verification of an Non-CT Based Total Knee Arthroplasty System for the LCS Prosthesis"; First Annual Meeting of the International Society for Computer Assisted Orthopedic Surgery, Davos, Switzerland, Feb. 8-10, 2001.

Martelli, et al., 'Criteria of interface evaluation for computer assisted surgery systems,' Int. J. Med. Informatics, 72:35-45 (2003).

Munoz, et al.: "Computer Assisted Planning of Hig Tibial Osteotomy for the Treatment of Knee Osteoarthritis"; http://www.utc.fr/esb/esb98/abs_htm/570.html, 3 pages.

Patent Abstracts of Japan, vol. 2002, No. 05, May 3, 2002 & JP 2002 017740A (Ochi Takahiro; Yonenobu Sakuo: MMT:KK); Jan. 22, 2002 (abstract).

Picard, et al.: "KneeNav—TKR: Concept and Clinical Application"; Computer Assisted Orthopedic Surgery USA 2000 Meeting, Pittsburgh, PA., Jun. 15-17, 2000.

Saragaglia, et al.: "Computer Assisted Total Knee Arthroplasty: Comparison with a Conventional Procedure. Results of a 50 Cases Prospective Randomized Study"; First Annual Meeting of the International Society for Computer Assisted Orthopedic Surgery, Davos, Switzerland, Feb. 8-10, 2001.

Simon, et al.: "The Fundamentals of Virtual Fluoroscopy," Medtronic Surgical Navigation Technologies, Medtronic, pp. 57-66; Computer Assisted Orthopedic Surgery USA 2000 Meeting, Pittsburgh, PA, Jun. 15-17, 2000.

Smith & Nephew Orthopaedics—"TriGen Reducer"; http://www.smithnephew.com/US/Standard.asp?NodeId=2996, 1 page (Jan. 21, 2003).

Smith & Nephew: "Surgical Technique—Mini Incision Hip—Posterior Approach," 20 pages, Mar. 2003 (brochure).

Smith & Nephew: "GENESIS II Total Knee System—Primary Surgical Technique," pp. 1-36 (Mar. 2001) (brochure).

Smith & Nephew Richards: "GENESIS® Total Knee System—Primary Surgical Technique—Anterior Referencing Instrumentation," pp. 1-59 (Dec. 1993) (brochure).

Smith & Nephew Richards: "GENESIS® Total Knee System—Surgical Technique Revision—Posterior Referencing Instrumentation," pp. 1-51 (Dec. 1993) (brochure).

Smith & Nephew Total Hip Replacement Surgery, HipReplacementInfo.com, 3 pages, Nov. 8, 2005 http://www/hipreplacementinfo.com/hip-total-replacement.htm.

Smith & Nephew Brochure, Design Features, "Opera" pp. 4-15 (1999).

Stryker Navigation System: Knee . . . best alignment for gap kinematics, 6 pages (2001) (brochure).

Sugano, et al.: "Medical Robotics and Computer-Assisted Surgery in the Surgical Treatment of Patients with Rheumatic Diseases"; http://www.rheuma21st.com/archives/cutting_edge_Robotics_Japan.html (Apr. 27, 2000).

Suhm, et al.: "Adapting the C-Arm Fluoroscope for Image Guided Orthopaedic Surgery"; CADS, pp. 212-214 (2002).

Tenbusch, et al.: "First Results Using the ROBODOC® System for Total Knee Replacement"; First Annual Meeting of the International Society for Computer Assisted Orthopedic Surgery, Davos, Switzerland, Feb. 7-10, 2001.

Valstar, et al.: "Towards Computer-Assisted Surgery in Shoulder Joint Replacement"; *ISPRS Journal of Photogrammetry & Remote Sensing*, 56:326-337 (2002).

Visarius, et al., 'Man-machine interfaces in computer assisted surgery,' Computer Aided Surgery, pp. 102-107 (2004).

National Institute of Arthritis and Musculoskeletal and Skin Diseases (NIAMS), 'Questions & Answers about . . . Knee Problems,'36 pp. (May 2001).

Merriam-Webster Online Dictionary, "Implant." Jan. 11, 2007 (1 page) www.m-w.com.

\* cited by examiner

IN-LINE MILLING SYSTEM

This application claims the benefit of U.S. Provisional Application Ser. No. 60/655,171, filed Feb. 22, 2005 titled "In-Line Milling System" and U.S. Provisional Application Ser. No. 60/730,184 filed Oct. 25, 2005 titled "In-Line Milling System," the entire contents of each of which are hereby incorporated by reference.

FIELD OF THE INVENTION

The present invention relates to devices, systems, and methods for use in milling a femoral canal, and specifically milling the proximal portion of the femur to receive an implant. Embodiments of the present invention provide a precise system and method to prepare a triangular cavity in bone into which a sleeve or body of a hip implant is positioned.

BACKGROUND

Hip replacement implants typically feature a stem with a head that cooperates with an acetabular cup. Hip stems are increasingly being provided in different sizes, lengths, and shapes. Some stems are also being provided with modular sleeves (also referred to as proximal bodies) that enable the stem to effectively "sit" in place with respect to the proximal femur. Sleeves or bodies in different sizes are provided to accommodate different bone structures and quality. The sleeves traditionally have a cone shape with a triangular spout extending from the cone, an example of which is shown by FIG. 7. The spouts approximate a portion of the proximal femur and provide additional support for the stem.

Preparing the proximal femur to receive a sleeve having a spout presents a challenge because bone must be removed in the shape of a triangle to receive the spout. In other words, once the distal femur has been reamed, a generally triangular shaped area needs to be milled out of the proximal reamer to receive the sleeve and spout. The surgeon should remove enough bone to achieve a secure fit, but not so much bone that the spout subsides and fails to support the stem as desired.

One previous preparation method has included aligning a shaft in the femoral canal and angling a cutter with respect to the shaft and moving the entire shaft within the canal to prepare the bone. An example of such a method is shown by FIG. 10 (which is reproduced from U.S. Pat. No. 5,002,578).

Another method has included aligning a shaft having an angled bearing in the femoral canal. A drill is inserted through the bearing at an angle to prepare a triangular cavity. An example of such a method is shown by FIG. 11 (which is reproduced from U.S. Pat. No. 5,540,694).

A variety of problems are encountered when using the methods and instrumentation of these procedures. For example, inserting a shaft into the canal and then separately inserting a drill through a bearing of the shaft causes the surgeon to have to maneuver multiple parts while also having to pay strict attention to the angles involved. One reason this causes a challenge is because the surgeon is holding the shaft at one angle (e.g., in the axis of the femoral canal) and maneuvering the drill at another angle (e.g., at an angle to form a triangular cut with respect to the axis of the canal), all while having to control the depth of the drilling. The surgeon often needs to drill the bone, remove the drill to check depth and shape of the cavity, and then reinsert the drill and continue the preparation. Although surgeons have become quite adept at these procedures, there is still a great deal of guess work involved. If too much bone is removed, the surgeon will often be forced to move to the next largest size of sleeve to accommodate for the excess bone removed.

Accordingly, it is desirable to provide more accurate milling methods that provide a precise cut. It is also desirable to provide a milling system that allows the surgeon to mill in a single direction, without having to enter the patient's leg at two different angles. (This is also beneficial to the patient because it is less invasive and a smaller incision can be used.) It is further desirable to provide a milling system that can be pre-assembled (e.g., on the back table by a nurse while the surgeon is preparing the site), which enables the milling to take place in one step. The systems and methods described herein provide many of these solutions.

SUMMARY

Embodiments of the present invention provide a milling system and method that provides a precise triangular cut in a patient's proximal femur. The system allows the surgeon to mill in a single direction, that is, the drill is in the same or similar longitudinal place as the handle of the milling system, preventing the surgeon from having to enter the patient's leg at two different angles. The present invention also provides a milling system that can be pre-assembled (e.g., on the back table by a nurse while the surgeon is preparing the site), which enables the milling to take place in one step, saving operating room time.

DETAILED DESCRIPTION OF THE DRAWINGS

Figure 7:
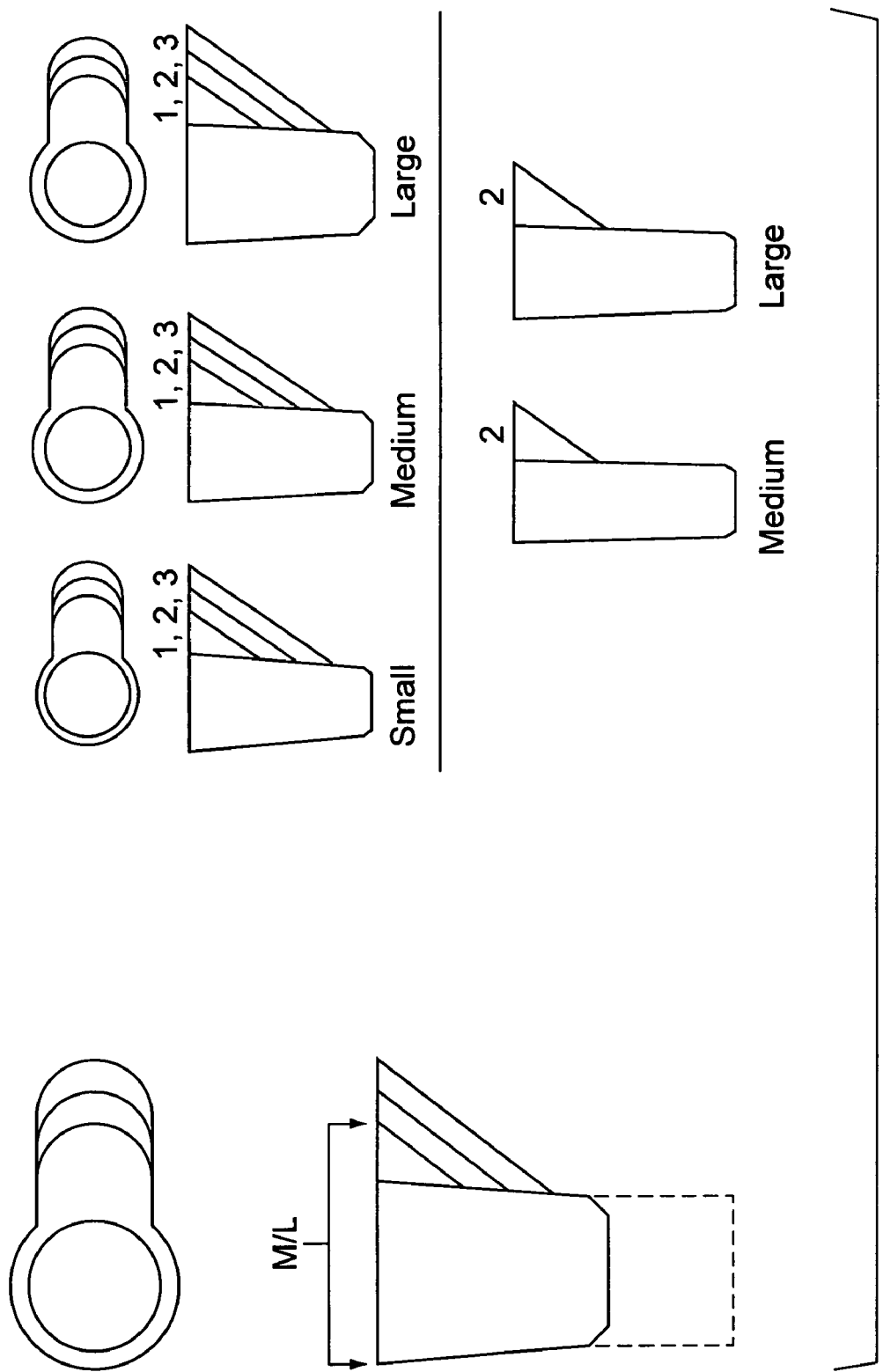
FIG. 7 shows various embodiments of proximal bodies (also referred to as sleeves with spouts) that may be used once a cavity has been milled using the systems described herein.

Embodiments of the present invention may be used to mill a triangular cavity in a proximal portion of a femur. Once the surgeon has prepared the distal portion of the femoral canal to receive a stem, he or she needs to prepare the proximal portion of the canal to receive the body of an implant. The triangular cavity to be prepared is shaped and sized to receive a triangular portion of a prosthetic hip implant, as shown in FIG. 7.

In preferred embodiments, unlike previous milling devices, the present invention does not require a component that slides laterally with respect to another component to mill the triangular cavity. Instead, the present invention allows the triangular cavity to be prepared using an in-line milling system that maintains the drill in the same or similar longitudinal plane as the handle of the support assembly. (Although the term "handle" is used throughout the specification and in the claims, it should be understood that an actual grasping portion is not required. The handle may be a rod, a stabilizing portion, or any other member that supports the drill receiving portion and drilling function.) Additionally, the in-line milling device, once assembled, may be inserted into the conically reamed femur cavity as a fixed unit to mill the triangular cavity. The surgeon is not required to insert one part of the assembly, locate the target area, and then insert a drill at an angle into the assembly.

Devices in accordance with embodiments of the present invention feature a milling handle 60, a milling body 40, and at least one cutting member 90. Examples of certain embodiments of these components, disassembled from one another, are shown in FIG. 1, although it is understood that other types of milling handles, milling bodies, and cutting members could also be used.

Figure 1:
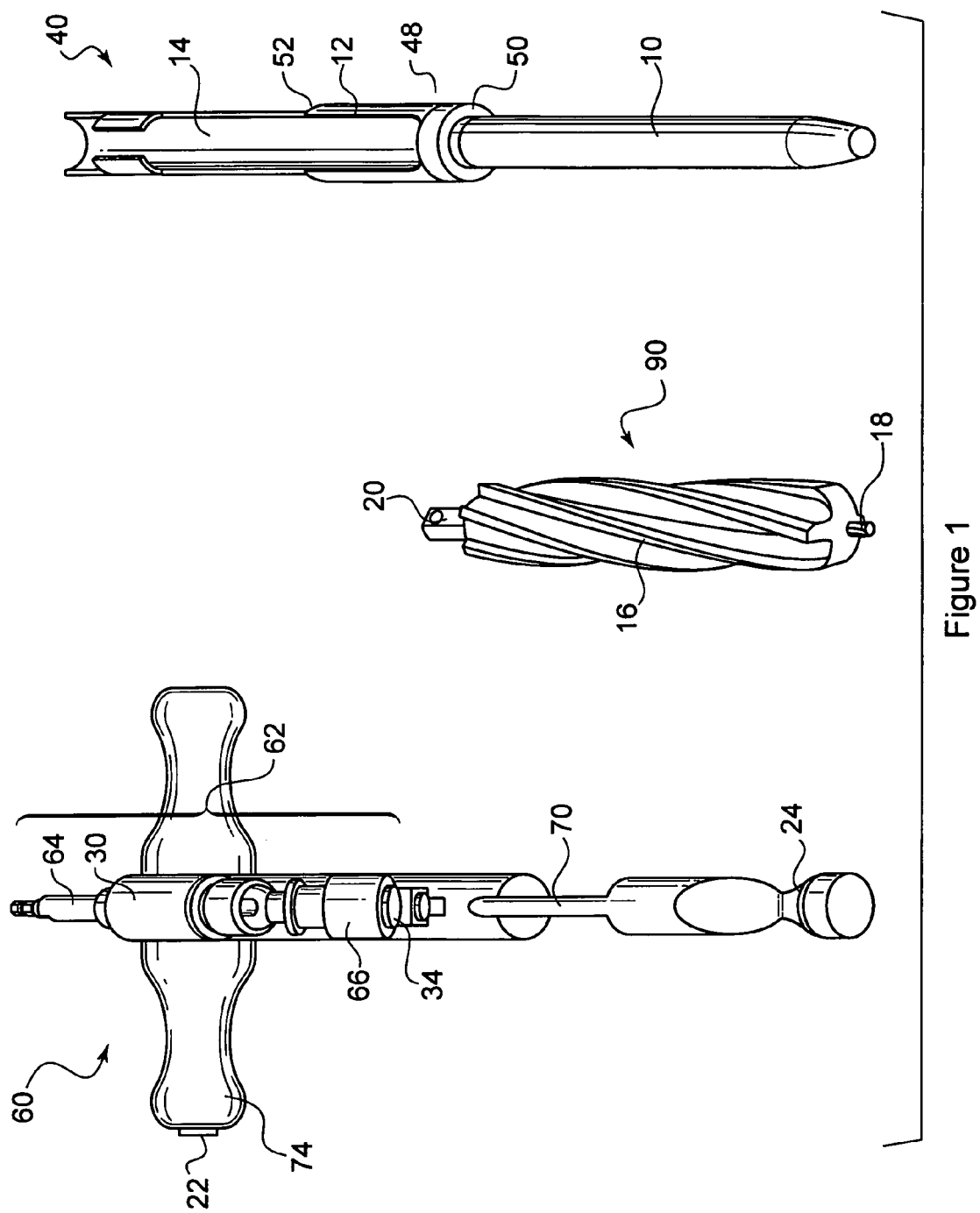
FIG. 1 shows a top perspective view of components of the milling system before assembly.
Figure 2:
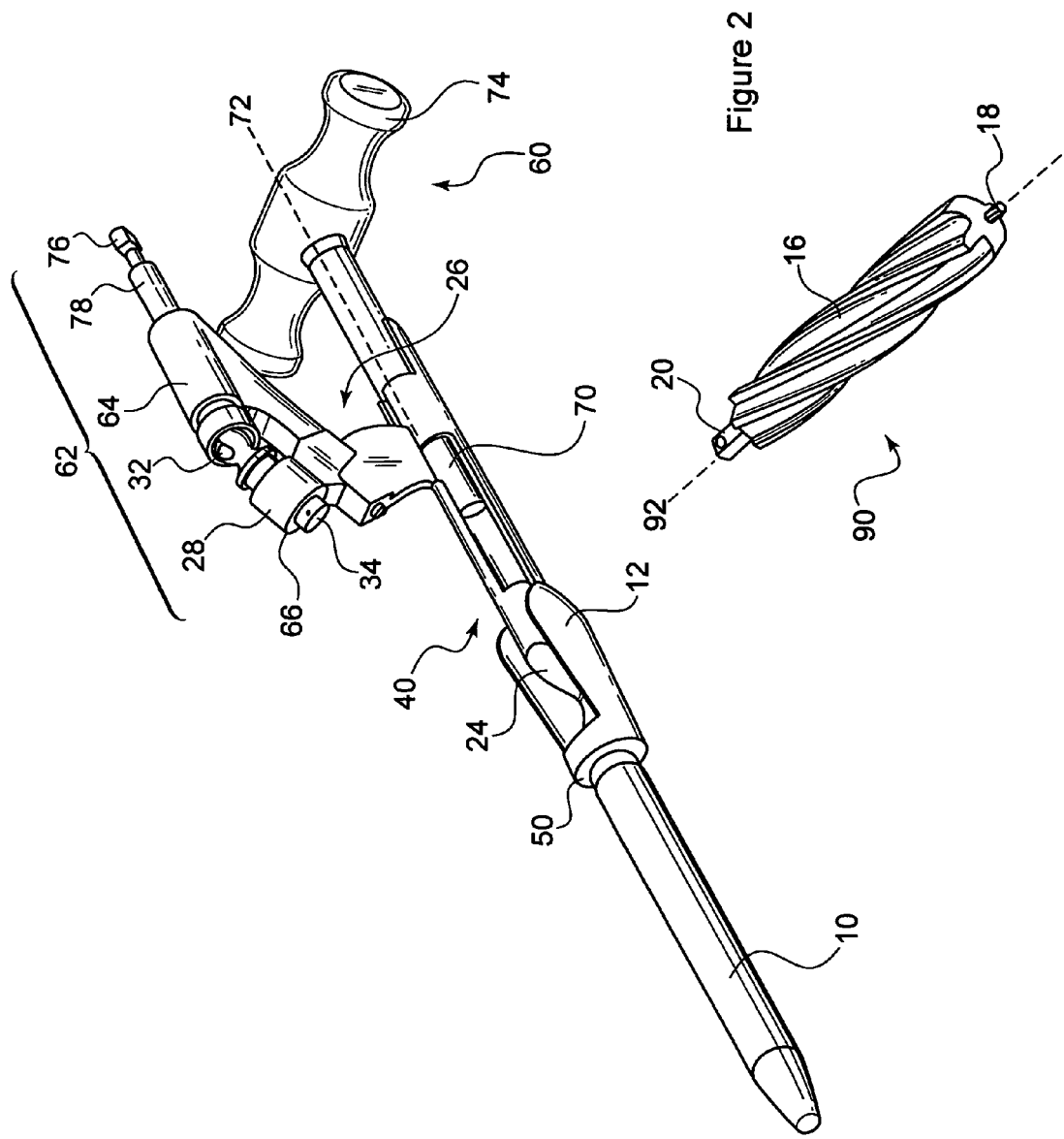
FIG. 2 shows the milling handle and milling body in an assembled position and the cutting member prior to its attachment.

The milling handle 60 shown in FIG. 1 includes a shaft 70, a drill directing portion 62, and a notched receiver 24. As shown in FIG. 2, the milling handle 60 has a shaft 70 with a longitudinal axis 72. At an upper end of the handle 60 is a handle grip 74. At the lower end is a notched receiver 24. The notched receiver 24 is adapted to provide a stop for the cutting member in use, as will be described more fully below.

Extending from the handle 60 is a drill directing portion 62. The drill directing portion 62 has a drill receiving end 78 and a cutting member receiving end 66. As shown in more detail in FIG. 2, the drill receiving end 78 has a chuck 76 near its distal tip and a shaft. The chuck 76 and shaft are attached to a bearing member 64, which is attached to a drive shaft 32, and in use, the chuck 76 receives a drill that rotates the bearing member 64 and drive shaft 32 to activate the cutting member. In certain embodiments, bearing member 64 is provided with plastic bushings to help rotation.

The cutting member receiving end 66 also has a bearing 28 that allows it to cooperate with the drive shaft 32 of drill receiving end 78 in order to rotate a cutting member. Cutting member receiving end 66 also has a socket 34 that receives a cutting member.

Figure 3:
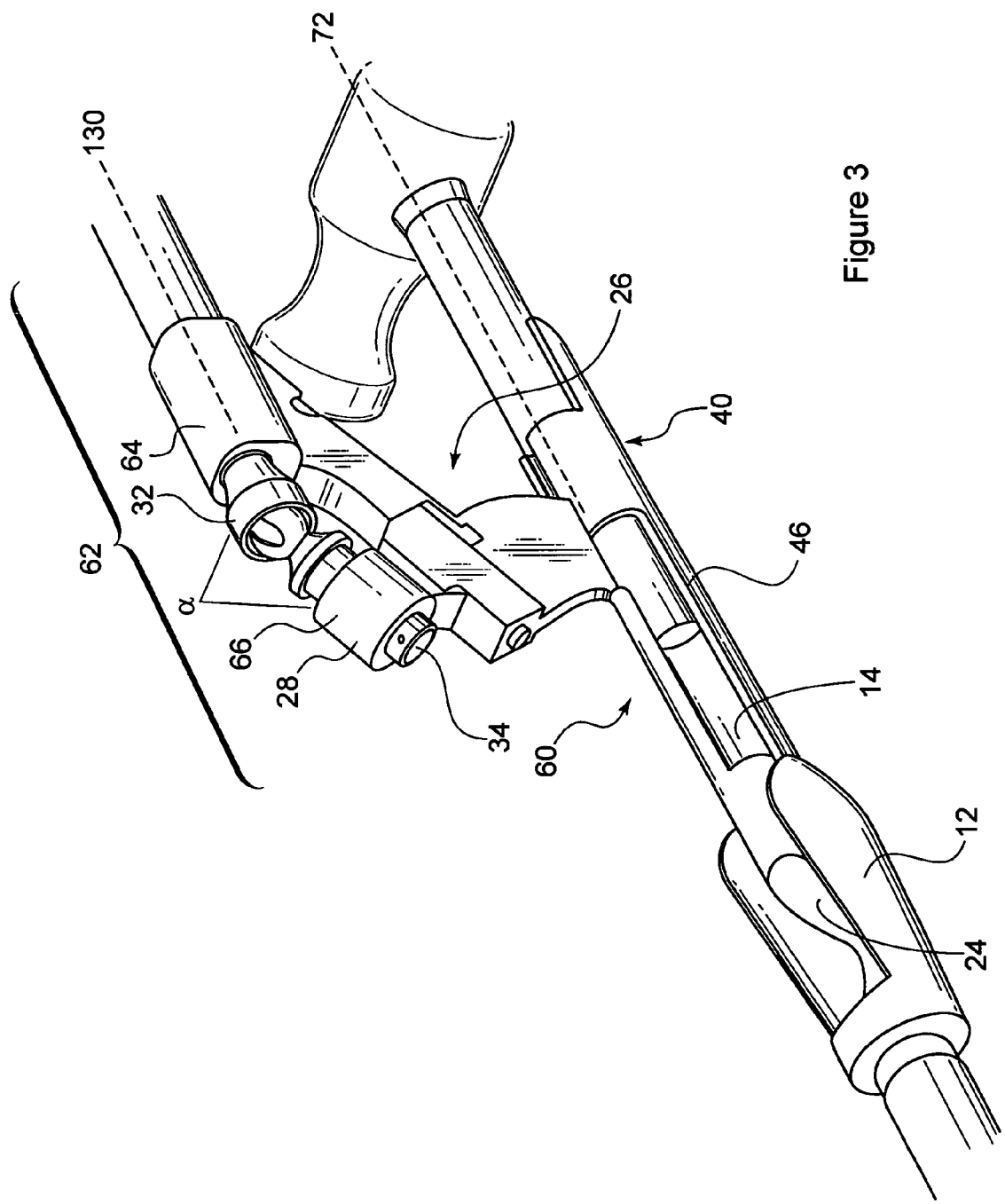
FIG. 3 shows a close up view of the assembly of FIG. 2.

As shown in FIG. 3, the drill receiving end 78 (which may be a one-piece component, but as discussed above, is preferably a multi-piece component with a chuck, a shaft, a bearing member, and a drive shaft) and the cutting member receiving end 66 are joined, connected, or otherwise associated with one another at an angle α. This angle allows two things to occur: (1) drill receiving end 78 has a longitudinal axis 130 that holds and receives a drill in line with the longitudinal axis 72 of the milling handle 60 and (2) the cutting member receiving end 66 receives a cutting member at an angle that can cut a triangular cavity. Referring back to FIG. 2, with respect the in-line drilling that is facilitated, when the drill is attached to the chuck 76, the drill receiving end 78 is configured so that pressure is applied in the direction of the longitudinal axis 72 of the handle 60 as the cavity is being milled. With respect to the angled cutting member, when the cutting member is attached to the cutting member receiving end 66, it is directed at an angle that allows the cutting member to form a triangular cavity at a very precise position and depth, which will be described in more detail below. One feature of handle 60 that allows the precise depth to be obtained is notched receiver 24, which acts as a stop to allow cutting member to form a precise cavity having the desired depth.

Figure 4:
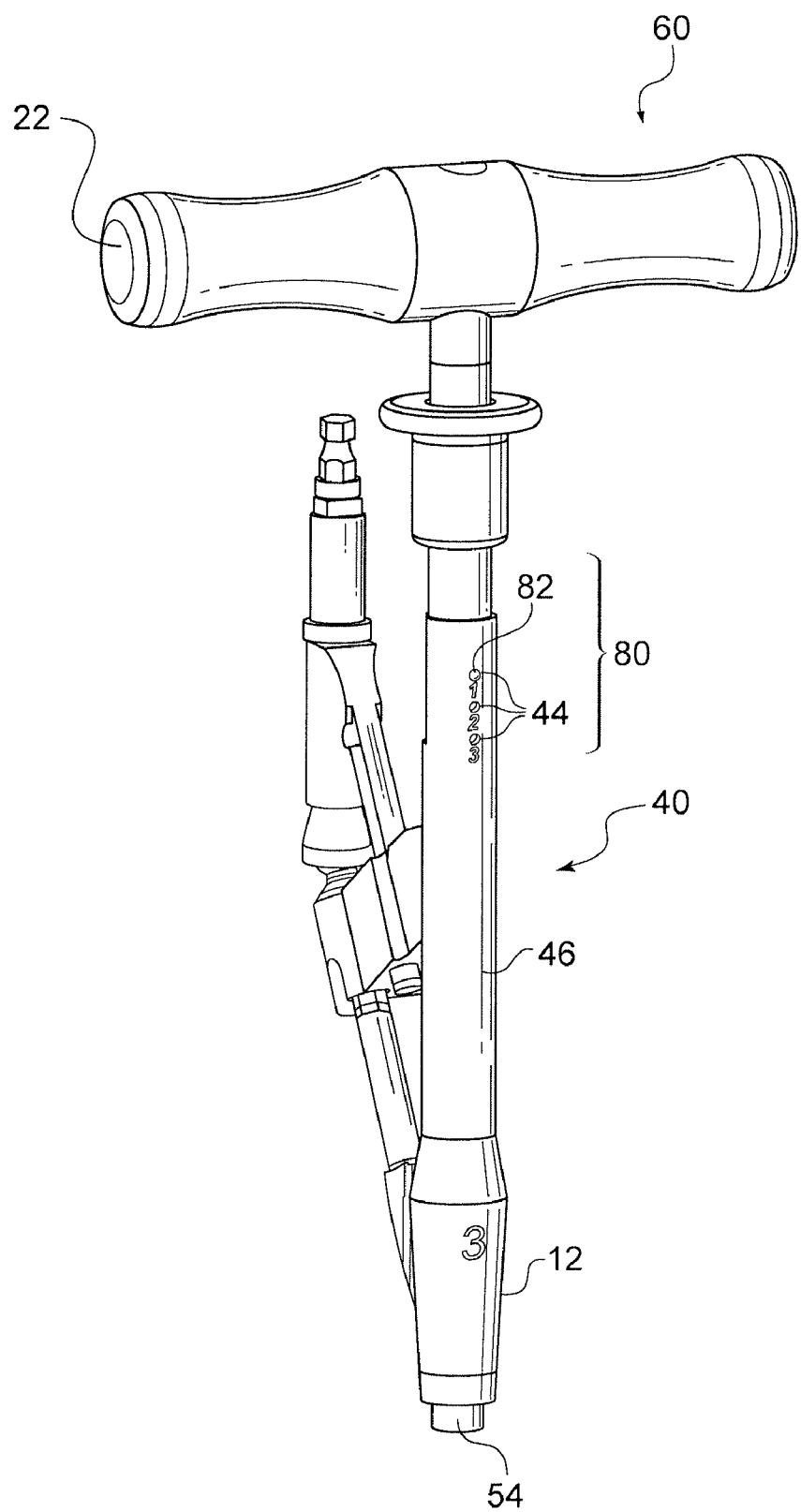
FIG. 4 shows a side perspective view of components of the milling system in a partially assembled configuration.

Referring back to the upper part of handle 60, there is also a securing member 80, as partially shown in FIG. 4. The securing member 80 serves to lock the milling body (described below) to the milling handle 60 in the desired position. In one embodiment, the securing member 80 is in the form of an actuator or a plunger that can be engaged with the user's index and middle finger to allow the securing to take place, by for example, a ball and detent mechanism. (The ball portion, which is shown with phantom line 82, of the ball and detent mechanism would be actuated by the plunger 80.)

Although not shown, it is possible to provide more than one ball and detent mechanism, which can help prevent damage to the instrument if the surgeon tries to impact the instrument during placement because it provides more attachment surface area. (It should be noted, however, that it is not desirable or necessary to impact the instrument during placement, but because some previous milling instruments have required impaction, some surgeons automatically use that as part of their milling method. It is thus desirable to provide an attachment mechanism that secures the handle and the milling body together in a secure manner that can withstand being impacted in use.) In another embodiment, the securing member 80 may be in the form of a button 22 on the side of handle (or anywhere on the handle or the handle of grip 74) that can be depressed to secure the components together. Other methods of securing two instruments together may also be used and will be described in more detail below, although non-limiting examples include a Morse taper, a J-lock configuration, a ratchet and receiver mechanism, an actuator, a cross bar and slot mechanism, or any other suitable connection method.

The description will now turn to the milling body 40, shown in FIG. 1. Milling body 40 preferably includes a pilot portion 10, a conical portion 12, and a channeled portion 14. The pilot portion 10 acts to guide the system into place in the femoral canal. In some embodiments, the pilot 10 acts as a stem for the system, stabilizing the system with respect to the already-prepared distal femur. The pilot portion 10 may be removable from milling body 40 (as described in more detail below) or it may be formed as an integral piece.

During preparation of the proximal femur, the surgeon uses a tool that creates a slight ledge on the proximal femur—this is the ledge that the conical portion 12 is adapted to abut. In other words, the conical portion 12 sits in a conically-shaped area prepared in the proximal femur when the system is in use. This prevents the system from being inserted too deeply into the femur and provides the most precise preparation possible. It bears mentioning here that some surgeons may or may not prepare the proximal femur with a ledge and the systems described herein may be used without such a ledge, but it is believed that providing a ledge helps ensure greater accuracy. The distal end 48 of the conical portion 12 preferably defines a ledge 50. The more proximal end 52 of the conical portion 12 has a slight flare, thus forming the conical shape of portion 12. This conical portion 12 is intended to correspond to the cone shaped implant (shown in FIG. 7) for which the cavity is being prepared. The ledge 50 at the distal end 48 is intended to "sit" where the end of the implant would sit, once implanted. In preferred embodiments, the outer profile of the conical portion 12 is sized about ½ mm smaller than the reamer that is used to prepare the proximal femur to allow the milling body 40 to slide in and out of the cavity easily and prevent it from sticking in place.

As shown in FIG. 4, in some embodiments, at the most distal end 48 of the milling body 40 there is provided a connection portion 54. Connection portion 54 is intended to allow the pilot portion 10 to be connected and removed from the milling body 40. In specific embodiments, connection portion 54 may be a protrusion that has screw threads that are received by a corresponding connection portion 56 on pilot 10 that is a threaded cavity. In other embodiments, the cavity and protrusion may be reversed. In further embodiments, the connection mechanism may be a Morse taper or any other mechanism that allows that body 40 and pilot 10 to be detachable. It should also be noted that providing this removability is preferred, but not required. If desired, milling body 40 may be provided as a one-piece component.

Figure 8:
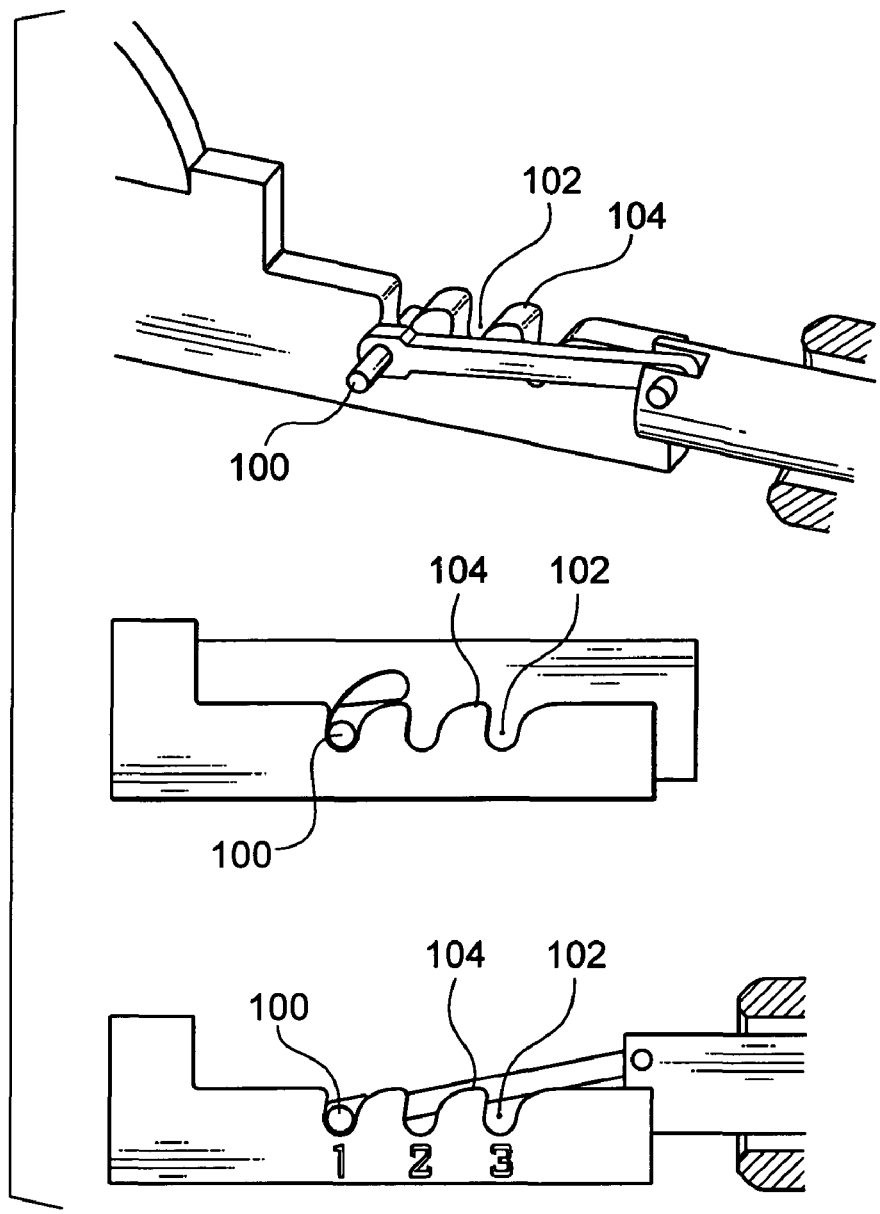
FIG. 8 shows one embodiment of a cross bar and slot connection mechanism between the milling handle and the milling body.
Figure 9:
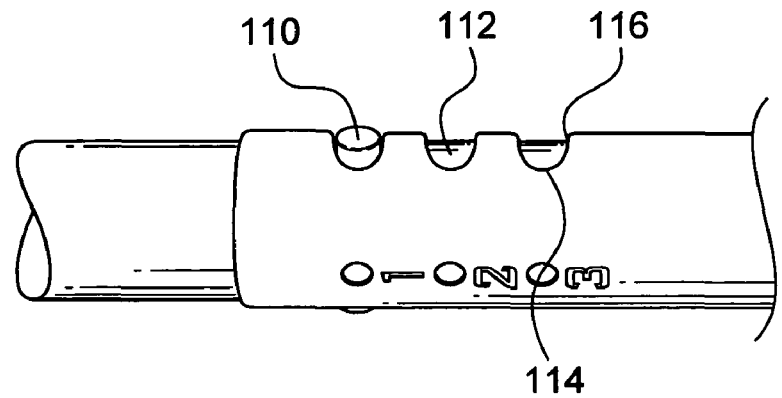
FIG. 9 shows an alternate connection mechanism between the milling handle and the milling body.
Figure 10:
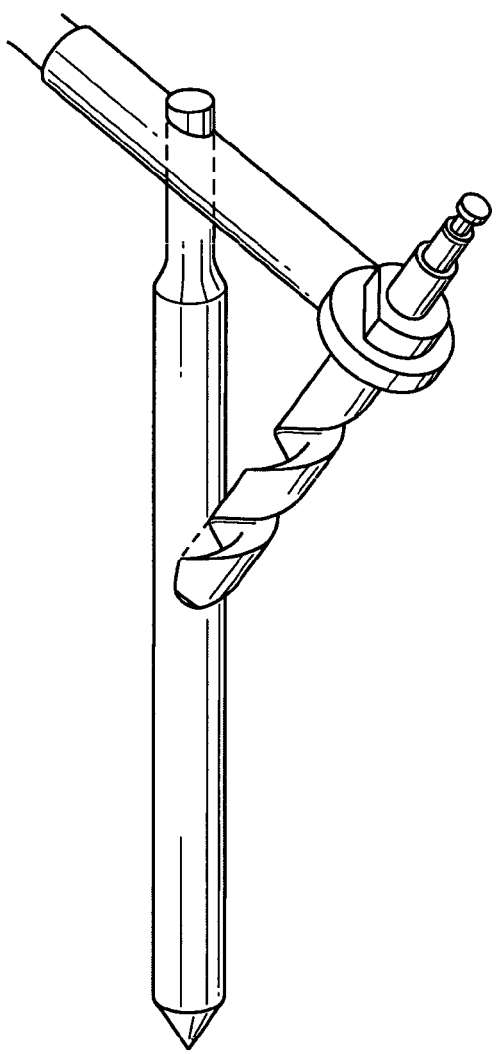
FIGS. 10 and 11 show prior art systems that have been used to mill triangular cavities.
Figure 11:
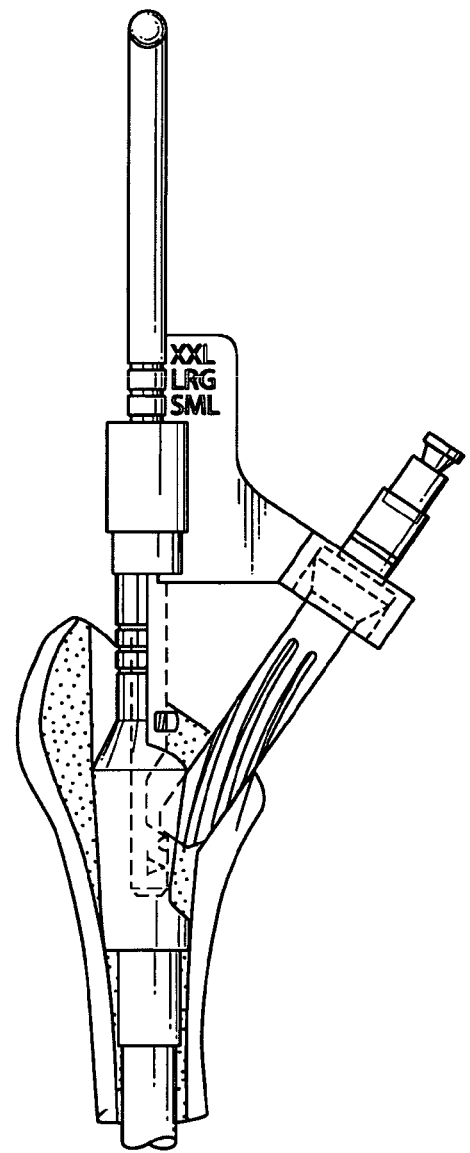

Milling body 40 also has a channeled portion 14 that forms the majority of its length. The channeled portion 14 of the milling body 40 is intended to receive the shaft 70 of the milling handle 60 in use. FIGS. 2 and 3 show the handle 60 and milling body 40 assembled together. In one embodiment, the shaft 70 of handle 60 slides into and is received by channeled portion 14. Although this configuration is preferred, it should be noted that handle 60 may have a channeled portion 14 and the milling body 40 may have the shaft 70. Additionally, although the channeled portion 14 is shown as partially open (e.g., not fully enclosed), it may be a hollow channel that is formed within the milling body 40. An alternate embodiment may also be to provide the milling handle and body with solid ends, one of which may have a series of ratchets or slots adapted to receive a cross bar, examples of which are shown in FIGS. 8 and 9, described below. Also, although the milling handle 60 and milling body 40 are described as two separate pieces (which is the preferred embodiment), it is also possible for the handle and body to be a one-piece component or for it to be more than two pieces.

As shown in FIG. 4, the channeled portion includes a corresponding securing member 42 that allows it to be secured to the milling handle 60. In some embodiments, the milling handle 60 securing member 80 is a ball 82 and the milling body 40 securing member is a series of detents 44 or recesses that receive the ball 82. The detents 44 are preferably located along the closed portion 46 of the channeled portion 14. It should be understood, however, that the location of the ball and/or detents may be changed, i.e., the ball could be on the milling body and the detent could be on the handle. In other embodiments, the securing members 80 and 42 are J-locks, where one securing member is a J-shaped channel and another securing member is a tab that is received in the J-shaped channel. A further embodiment that may be used to secure handle 60 to body 40 is a series of Morse tapers of different sizes. One securing member could be a cone shaped receiving member and another could be a tapered portion that engages therewith. In order to provide the desired interchangeability to accommodate the preparation of a cavity that can receive different sizes of sleeves, the taper portion could be removable and different tapers could be provided. The tapers could screw onto the milling body or the handle. Alternatively, the portions could screw to one another without the use of a taper.

An even further embodiment is a ratchet and receiver mechanism or a gate-lock type mechanism. One example of a ratchet and receiver embodiment is shown in FIG. 8. In this embodiment, the handle or the milling body has a ratchet 100 (e.g. a T-shaped lever), and the other has a series of receivers 102. The receivers may have curved edges 104 that secure the ratchet 100 in place and prevent it from sliding out. More than one receiver 102 is preferably provided to allow for adjustability in size. A gate-lock type mechanism (e.g., a sliding member that closes over the ratchet 100 once in place to prevent it from sliding out, similar to the sliding member that closes over a gate to prevent it from being blown open by wind) may also be provided.

A further embodiment is shown in FIG. 9, which details how a cross bar 110 (or ratchet) may be received in indentations 112. Indentations may have curved edges, similar to those shown in FIG. 8, or they may have curved bases 114 only, with their sides and tips 116 extending up in a U-shaped configuration. There are preferably as many cross bars 110 and indentation 112 options as there are sizes to be provided.

Although a few alternate embodiments for securing members have been described, it should be understood that any connection member that allows handle 60 and milling body 40 to be removably attached to one another in different configurations to allow for preparation of a cavity of a different size is considered within the scope of this invention. If body and handle are provided as a single piece, there should be some feature that allows them to expand and retract in size relative to one another to allow for the adjustability options described herein.

For the remainder of this description, the ball and detent securing mechanism will be described as the structure used to secure the handle 60 to the milling body 40. In the preferred embodiment for this configuration, the ball 82 is located on an upper area of the handle 60 and the recess or detent 44 is located on an upper area of the milling body 40. However, these locations may be changed (e.g., to be elsewhere on each component) or the ball 82 may be on the milling body 40 and vice versa. During use, the ball is depressed 82 and allowed to be released within one of the detents 44 to secure the components.

In a particularly preferred embodiment, there are provided multiple detents 44 that enable ball 82 to be received in multiple configurations. (If another securing mechanism is used, it is preferred that that mechanism also allow various positioning options.) Some embodiments may have three detents 44, as shown in FIG. 4. These detents 44 allow handle 60 to be positioned at three different depths, allowing the triangular cavity to be prepared in three different depths to accommodate one of three differently sized implants or sleeves. Although three sizing options are described and are typically preferred, it is also possible to provide only one option or to provide many more options, depending upon the complication and detail for ease of reference. There may simply be provided 5 or 8 or 10 (or any number) of detents that may receive the ball 82.

The cutting member 90 shown in FIG. 1 includes cutting surface 16, distal pin 18 and shank 20. Cutting member 90 also has a central axis 92 that extends through cutting member 90. Cutting surface 16 may be a blade, a drill bit-type surface, or any other surface used to cut bone. In use the shank 20 is received by the cutting member receiving end 66 of the drill directing portion 62. The distal pin 18 is received by notched receiver 24 of the milling handle 60. This secures the cutting member 90 in place and provides a very accurate cut. One of the benefits of the system described herein is that it prevents the guesswork that is commonly required for preparing a triangular cavity to receive a sleeve with a spout.

Method:

Once the surgeon has reamed the distal femur and prepared the proximal portion of the femur, he or she will need to prepare a triangular cavity to receive the proximal body (also referred to as a sleeve with a spout). It is preferred to use a proximal body that corresponds to the size of the stem diameter. (In other words, if the surgeon is using a 15 mm stem, he or she will want to select a proximal body that cooperates with that stem and has a similar diameter).

The proximal bodies for use with the systems described herein are preferably color coded and provided with a system that makes choosing the proximal body (and thus, the size of the triangular cavity to be prepared) quite effortless. For example, all 15 mm bodies may be colored green and all 13 mm bodies may be yellow. One factor to be considered is the diameter of the body (selected to correspond to the stem), and the other two factors are the extension of the spout and the height/thickness of the body. These other two factors can be simplified by using the preferred proximal body system for use with the milling system of this invention.

As shown in FIG. 7, the bodies are provided in spout sizes 1, 2, and 3 and the size of the bodies are small, medium, and large. These examples are provided only to help the reader visualize the various types of proximal bodies that can be used and they are in no way intended to be limiting. Alternate sizes may be provided in any other appropriate manner, such as using a lettering system (A, B, and C) or a naming system (such as Alpha, Bravo, Charlie), and so forth. FIG. 7 also shows that it is possible to provide standard sized bodies, as well as tall bodies (shown in phantom lines). However, for the ease of this description, the preferred system shown in FIG. 7 will be referred to throughout the remainder of this section.

The surgeon will typically prepare the proximal femur to receive the size of proximal body selected, for example, a small, medium or large. In order to prepare an appropriate triangular cavity, however, the surgeon will need to prepare a triangular cavity that corresponds to either the 1, 2, or 3 position of the spout. That is where the milling system according to certain embodiments of the present invention is particularly useful.

In use, the in-line milling system is completely assembled prior to insertion into the femur cavity. First, the milling handle 60 is assembled to the milling body 40 in one of three different lengths using the securing members 42 and 80. In a preferred embodiment, the members are provided in options of 1, 2, or 3, corresponding to the size of the proximal body to be used. (However, it should again be understood that any number of options may be provided.) In a particularly preferred embodiment, the securing members are a ball 82 on the handle 60 that engages one of the three small detents 44 in the closed portion 46 of the channeled portion 14 of the milling body 40 to lock the milling handle 60 member at the desired length.

The surgeon selects the length of the instrument depending on how large a triangular cavity he or she desires to mill, which depends upon the size of the patient, the size of the femur, and the depth and width of the canal formed within the femur. Increasing the length of the instrument decreases the size of the triangular cavity that will be milled. So, for example, if a "small" body with a "1" spout is to be used, the handle 60 and body 40 will be attached to one another at the "1" configuration.

Figure 5:
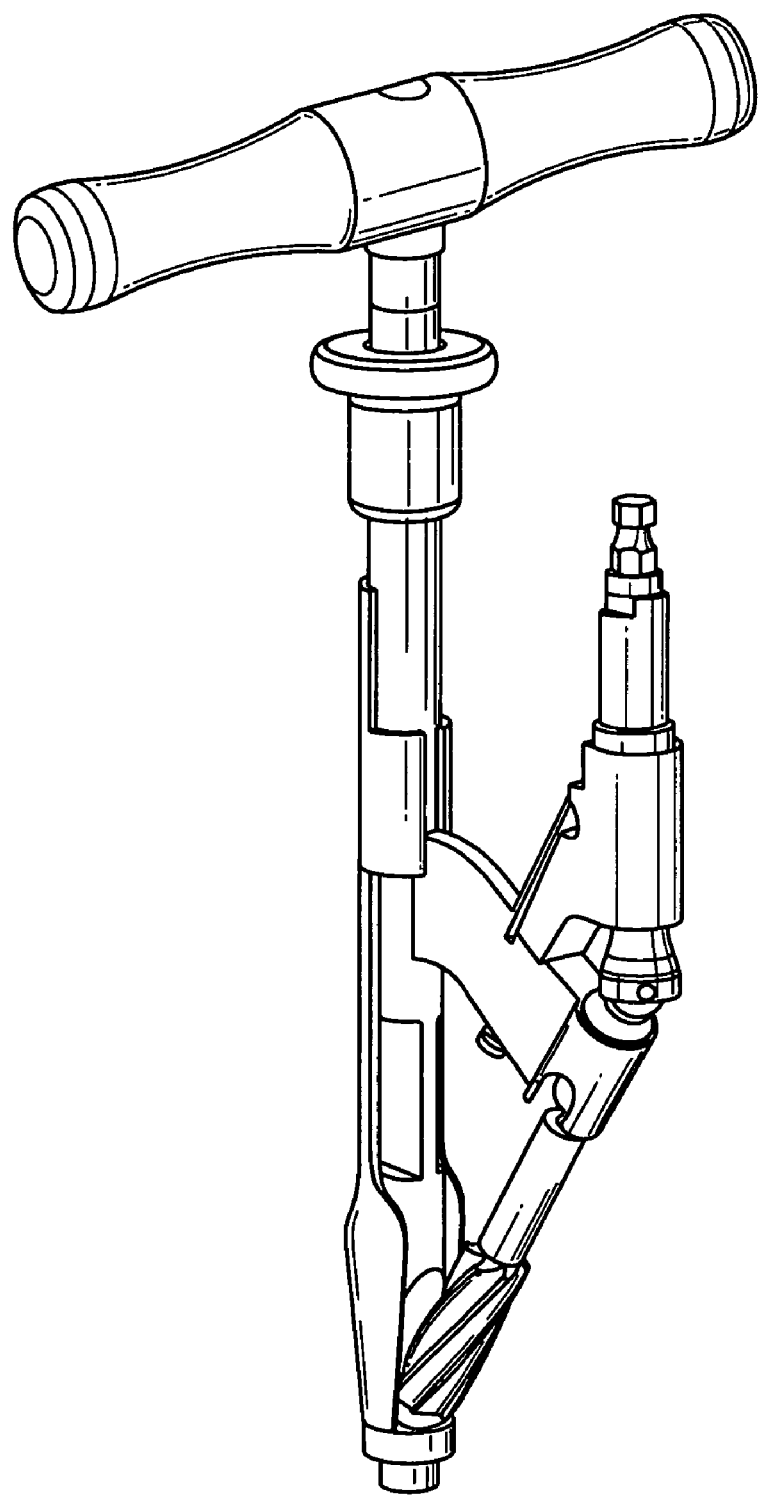
FIG. 5 shows another perspective of the assembly of FIG. 4.
Figure 6:
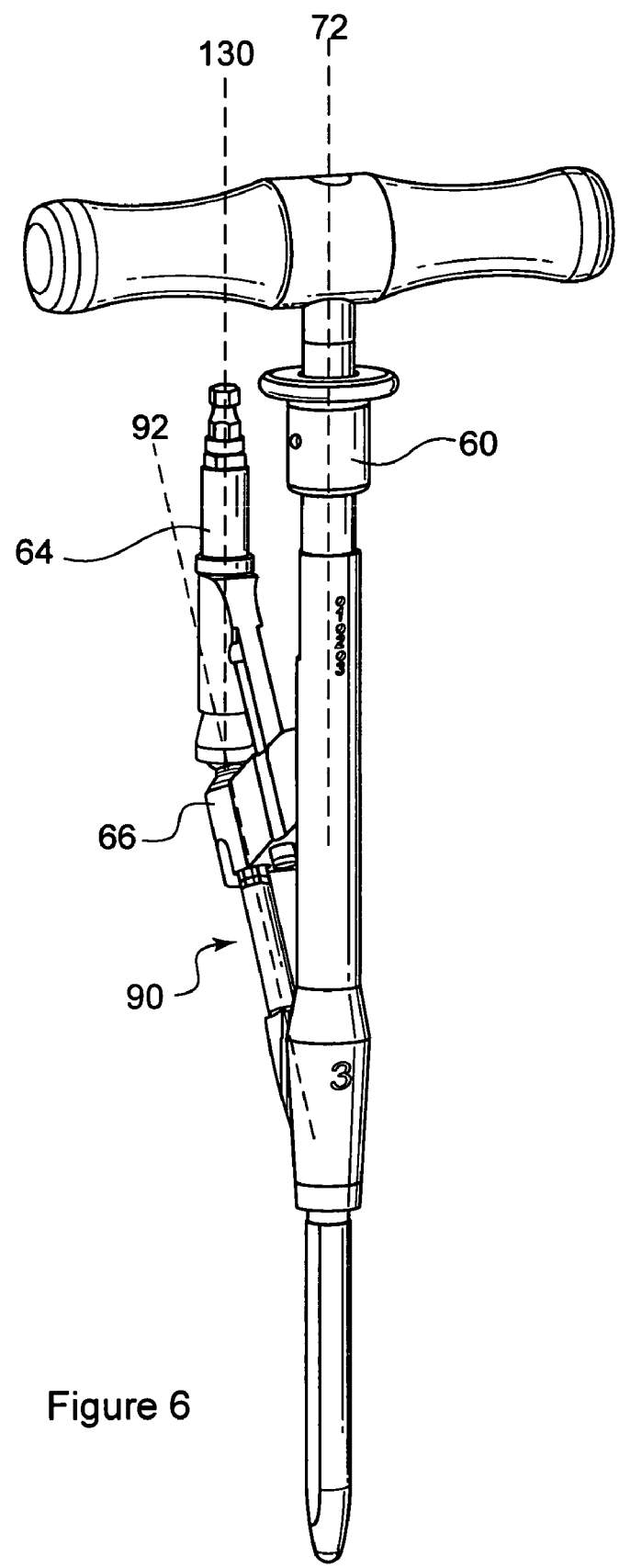
FIG. 6 shows another perspective of the assembly of FIG. 4, showing orientation lines.

Once the milling handle 60 is locked into the milling body 40 at the desired length, as shown in FIGS. 2 and 3, the cutting member 90 is secured to the instrument, as shown in FIGS. 4-6. If not already connected, the pilot member 10 should be attached to the connection portion 54 to complete assembly of the instrument, as shown in FIG. 6.

The distal pin 18 on the cutting member 90 fits into a hole in the notched receiver 24, as shown in FIG. 5. The cutting member's shank 20 fits into the socket 34, which cooperates with the drive shaft 32. The cutting member 90 is secured by sliding the locking member 26 slightly distally to fully engage the cutting members' shank in the socket 34. FIGS. 2 and 3 show the locking member 26 in an unlocked orientation and FIGS. 5 and 6 show the locking member 26 in a locked position. Locking member 26 may be adapted to slide up and down the handle, it may be adapted to move and lock independently of the handle, or both. One preferred way that locking member 26 locks is via a bayonet lock, although it should be understood that any locking method may be used. Once the cutting member 90 is secured, rotation of the drive shaft rotates the cutting member. The drive shaft, not the cutting member, is supported by bearing 28.

In use, the surgeon inserts the instrument into the reamed cavity as an electric motor rotates the drive shaft 32 and cutting member 90. The surgeon continues to insert the instrument, milling the triangular cavity in the process, until the conical portion 12 of the milling body 40 contacts the walls of the conically reamed cavity in the femur. At that point, the milling is completed. If the surgeon desires to enlarge the triangular cavity, he or she may shorten the length of the instrument (consequently allowing the cutting member to penetrate deeper into the femur) and re-mill the cavity.

The instruments and methods described above may also be used in connection with computer assisted surgery techniques, devices, and methods. For example, a reference marker, such as a reference fiducial described in co-pending U.S. patent application Ser. No. 10/897,857 filed Jul. 23, 2004 entitled "Surgical Navigation System Component Fault Interfaces and Related Processes" and U.S. patent application Ser. No. 10/689,103 filed on Oct. 20, 2003 (both of which are hereby incorporated by this reference) may be used to identify the location on the patient's hip to be prepared. Specifically, a reference marker or fiducial may be used to identify the greater trochanter, the lesser trochanter, the center of the canal, and/or other portions along the canal to identify where the center of the head should be located. This would allow a computer to create a three-dimensional representation of the surgical site. This can be useful in either (a) assisting the surgeon in choosing the appropriately sized implant to use and/or (b) using a computer to control the milling instruments described to prepare a cavity of the desired depth and size.

Changes and modifications, additions and deletions may be made to the structures and methods recited above and shown in the drawings without departing from the scope or spirit of the invention and the following claims.

What is claimed is:

1. An in-line milling system for use with a cutting member, comprising:
    (a) a milling handle having a longitudinal axis;
    (b) a milling body adapted to be positioned at least partially within a bone, wherein the milling body comprises a channeled portion adapted to receive the milling handle such that the milling handle can translate within the milling body;
    (c) a securing system configured to lock the milling handle to the milling body in at least one pre-determined position to prevent relative translation between the milling body and the milling handle; and
    (d) a drill directing joint associated with the milling handle and comprising a drill receiving portion having an end adapted to receive a drill substantially parallel with the longitudinal axis of the milling handle and a cutting member receiving portion connected at an angle to the drill receiving portion and having an end adapted to receive the cutting member such that the cutting member extends along an axis that is not parallel to the longitudinal axis of the milling handle; wherein the drill receiving portion and the cutting member receiving portion remain connected at the angle to form an angled joint when the cutting member is not secured to the end of the cutting member receiving portion.

2. The in-line milling system of claim 1, wherein the drill receiving portion comprises a rotatable shaft, wherein the cutting member receiving portion comprises a rotatable shaft, and wherein, in use, a drill attached to the end of the drill receiving portion rotates both the rotatable shaft of the drill receiving portion and the rotatable shaft of the cutting member receiving portion in order to rotate the cutting member.

3. The in-line milling system of claim 2, wherein the cutting member receiving portion comprises an axis, wherein the axis of the cutting member receiving portion and the axis of the cutting member substantially align, and wherein the cutting member receiving portion is adapted to apply torque about the axis of the cutting member.

4. The in-line milling system of claim 1, wherein the securing system is configured to lock the milling handle to the milling body in one of multiple pre-determined positions to prevent relative translation between the milling body and the milling handle.

5. The in-line milling system of claim 1, wherein the securing system comprises a ball and detent mechanism.

6. The in-line milling system of claim 1, wherein the securing system comprises a cross bar and indentation mechanism.

7. The in-line milling system of claim 6, wherein the cross bar and indentation mechanism comprises at least one indentation located on one of the milling handle and the milling body and a cross bar associated with the other of the milling handle and the milling body.

8. The in-line milling system of claim 7, wherein the at least one indentation is located on the milling body and wherein the cross bar is associated with the milling handle.

9. The in-line milling system of claim 1, wherein the securing system comprises a bayonet and curved receiver mechanism.

10. The in-line milling system of claim 1, wherein the angle is a fixed angle.

11. The in-line milling system of claim 1, wherein the axis of the cutting member is substantially straight.

12. The in-line milling system of claim 1, wherein each of the drill receiving portion and the cutting member receiving portion comprises a first end and a second end, wherein the first end of the drill receiving portion is adapted to receive the drill and the second end of the cutting member receiving portion is adapted to receive the cutting member and wherein the second end of the drill receiving portion and the first end of the cutting member receiving portion are connected at the angle.

13. An in-line milling system for use with a cutting member having a substantially straight axis, the system comprising:
(a) a milling handle having a shaft with a longitudinal axis;
(b) a milling body adapted to be positioned at least partially within a bone, wherein the milling body comprises a channeled portion adapted to receive the milling handle such that the milling handle can translate within the milling body;
(c) a drill directing portion associated with the milling handle, the drill directing portion comprising a drill receiving portion and a cutting member receiving portion having an axis, the drill receiving portion and the cutting member receiving portion connected to one another to form an angled joint such that the drill receiving portion is configured to receive a drill in parallel with the longitudinal axis of the milling handle and the cutting member receiving portion is configured to receive the cutting member such that the axes of the cutting member and the cutting member receiving portion are substantially co-linear and are not parallel to the longitudinal axis of the milling handle; and
(d) a securing system configured to lock the milling handle to the milling body in at least one pre-determined position to prevent relative translation between the milling body and the milling handle.

14. The in-line milling system of claim 13, wherein the drill receiving portion comprises a rotatable shaft, wherein the cutting member receiving portion comprises a rotatable shaft, and wherein, in use, a drill attached to the end of the drill receiving portion rotates both the rotatable shaft of the drill receiving portion and the rotatable shaft of the cutting member receiving portion in order to rotate the cutting member.

15. The in-line milling system of claim 14, wherein the cutting member receiving portion is adapted to apply torque about the axis of the cutting member.

16. The in-line milling system of claim 13, wherein the securing system is configured to lock the milling handle to the milling body in one of multiple pre-determined positions to prevent relative translation between the milling body and the milling handle.

17. The in-line milling system of claim 13, wherein the securing system comprises a cross bar and indentation mechanism.

18. The in-line milling system of claim 17, wherein the cross bar and indentation mechanism comprises at least one indentation located on one of the milling handle and the milling body and a cross bar associated with the other of the milling handle and the milling body.

19. The in-line milling system of claim 18, wherein the at least one indentation is located on the milling body and wherein the cross bar is associated with the milling handle.

20. The in-line milling system of claim 13, wherein the securing system comprises a ball and detent mechanism.

21. The in-line milling system of claim 13, wherein the securing system comprises a bayonet and curved receiver mechanism.

22. The in-line milling system of claim 13, wherein the drill receiving portion and the cutting member receiving portion remain connected at the angled joint when the cutting member is not secured to the cutting member receiving portion.

23. The in-line milling system of claim 13, wherein the angled joint retains the drill receiving portion and the cutting member receiving portion at a fixed angle.

24. A method for preparing a bone for receiving an implant comprising:
(a) providing a milling system comprising: (i) a milling handle having a longitudinal axis; (ii) a milling body adapted to be positioned at least partially within the bone and comprising a channeled portion adapted to receive the milling handle such that the milling handle can translate within the milling body; (iii) a cutting member; and (iv) a drill directing portion associated with the milling handle and comprising a drill receiving portion and a cutting member receiving portion having an axis, the drill receiving portion and the cutting member receiving portion connected to one another to form an angled joint, such that the drill receiving portion is configured to receive a drill substantially parallel with the longitudinal axis of the milling handle and the cutting member receiving portion is configured to receive the cutting member such that the cutting member extends along an axis that is not parallel to the longitudinal axis of the milling handle;
(b) assembling the milling system by (i) inserting the milling handle into the channeled portion of the milling body; (ii) locking the milling handle and the milling body together to prevent relative translation between the milling handle and the milling body; and (iii) securing the cutting member to the cutting member receiving portion of the drill directing portion such that the axis of the cutting member and the axis of the cutting member receiving portion are substantially co-linear;

(c) inserting the assembled milling system into the bone; and (d) activating the drill to rotate the cutting member to form a triangular-shaped cavity in the bone.

25. The method of claim 24, wherein locking the milling handle and the milling body together to prevent relative translation between the milling handle and the milling body comprises inserting a cross bar associated with one of the milling handle and the milling body into at least one indentation located on the other of the milling handle and the milling body.

26. The method of claim 25, wherein the at least one indentation comprises a plurality of indentations and wherein the method further comprises disengaging the cross bar from the at least one indentation, translating the milling handle and the milling body relative to each other, and inserting the cross bar into another of the indentations.

27. The method of claim 25, wherein the cross bar is associated with the milling handle and wherein the at least one indentation is located on the milling body.

28. A method for preparing a bone for receiving an implant comprising:
(a) selecting from a plurality of implants having a triangular-shaped portion an implant having a desired size;
(b) providing a milling system comprising: (i) a milling handle having a longitudinal axis; (ii) a milling body adapted to be positioned at least partially within the bone and comprising a channeled portion adapted to receive the milling handle such that the milling handle can translate within the milling body; (iii) a cutting member; and (iv) a drill directing portion associated with the milling handle and comprising a drill receiving portion and a cutting member receiving portion, wherein the drill receiving portion is configured to receive a drill substantially parallel with the longitudinal axis of the milling handle and the cutting member receiving portion is configured to receive the cutting member such that the cutting member extends along an axis that is not parallel to the longitudinal axis of the milling handle, wherein the drill receiving portion and the cutting member receiving portion remain connected at an angle to form an angled joint when the cutting member is not secured to the cutting member receiving portion;
(c) assembling the milling system by (i) inserting the milling handle into the channeled portion of the milling body; (ii) selecting from at least two pre-determined relative positions of the milling handle and the milling body the desired relative position of the milling handle and the milling body based at least partially on the desired size of the implant and locking the milling handle and the milling body in the desired pre-determined relative position to prevent relative translation between the milling body and the milling handle; and (iii) securing the cutting member to the cutting member receiving portion such that the cutting member extends along an axis that is not parallel to the longitudinal axis of the milling handle;
(d) inserting the assembled milling system into the bone; and
(e) activating the drill to rotate the cutting member to form a triangular-shaped cavity in the bone.

29. The method of claim 28, wherein locking the milling handle and the milling body in the desired pre-determined relative position to prevent relative translation between the milling body and the milling handle comprises inserting a cross bar associated with one of the milling handle and the milling body into one of at least two indentations located on the other of the milling handle and the milling body, wherein each of the at least two indentations represents one of the at least two pre-determined relative positions.

30. The method of claim 29, wherein the cross bar is associated with the milling handle and wherein the at least two indentations are located on the milling body.

31. The method of claim 29, further comprising disengaging the cross bar from the one of the at least two indentations, translating the milling handle and the milling body relative to each other, and inserting the cross bar into another of the at least two indentations.

32. An in-line milling system for use with a cutting member comprising:
(a) a milling handle having a shaft with a longitudinal axis;
(b) a milling body adapted to be positioned at least partially within a bone, wherein the milling body comprises a channeled portion adapted to receive the milling handle such that the milling handle can translate within the milling body;
(c) a drill directing portion associated with the milling handle, the drill directing portion comprising a drill receiving portion having an end and a cutting member receiving portion having an end, wherein the drill receiving portion end is adapted to receive a drill in parallel with the longitudinal axis of the milling handle, and the cutting member receiving portion end is adapted to receive the cutting member such that the cutting member extends along an axis that is not parallel with the longitudinal axis of the milling handle, wherein the drill receiving portion and the cutting member receiving portion remain connected at an angle to form an angled joint when the cutting member is not secured to the cutting member receiving portion end; and
(d) a securing system adapted to rigidly lock the milling handle to the milling body in at least one pre-determined position to prevent relative translation between the milling body and the milling handle.

33. An in-line milling system for use with a cutting member comprising:
(a) a milling handle having a shaft with a longitudinal axis;
(b) a milling body adapted to be positioned at least partially within a bone, wherein the milling body comprises a channeled portion adapted to receive the milling handle such that the milling handle can translate within the milling body; and
(c) a drill directing portion associated with the milling handle, the drill directing portion comprising a drill receiving portion and a cutting member receiving portion,
wherein the drill receiving portion is adapted to receive a drill in parallel with the longitudinal axis of the milling handle and the cutting member receiving portion is adapted to receive the cutting member at an angle that is not parallel with the longitudinal axis of the milling handle, wherein the drill receiving portion and the cutting member receiving portion remain connected at an angle to form an angled joint when the cutting member is not secured to the cutting member receiving portion, and wherein the cutting member receiving portion is adapted to apply torque about a substantially straight axis shared by both the cutting member receiving portion and a cutting member in use; and
(d) a securing system configured to lock the milling handle to the milling body in at least one pre-determined position to prevent relative translation between the milling body and the milling handle.

34. A method for preparing a bone for receiving an implant comprising:

(a) providing an in-line milling system comprising: (i) a milling handle having a longitudinal axis; (ii) a milling body adapted to be positioned at least partially within the bone and having a length and a channeled portion adapted to receive the milling handle such that the milling handle can translate within the milling body; (iii) a drill directing portion associated with the milling handle and comprising a drill receiving portion and a cutting member receiving portion adapted to receive a cutting member such that the cutting member is oriented at an angle relative to the longitudinal axis of the milling handle, wherein the drill receiving portion and the cutting member receiving portion remain connected at an angle to form an angled joint when the cutting member is not secured to the cutting member receiving portion;

(b) inserting the milling handle into the channeled portion of the milling body;

(c) selecting from a plurality of pre-determined relative positions of the milling handle and the milling body the desired relative position of the milling handle and the milling body and locking the milling handle and the milling body in the desired pre-determined relative position by inserting a cross bar associated with the milling handle into one of a plurality of indentations located along the length of the milling body;

(d) inserting the milling system into the bone; and (e) activating a drill to rotate the cutting member to form a triangular-shaped cavity in the bone.

35. The method of claim 34, further comprising disengaging the cross bar from the one of the plurality of indentations, translating the milling handle and the milling body relative to each other, and inserting the cross bar into another of the plurality of indentations.

36. An in-line milling system for use with a cutting member, comprising:

(a) a milling body adapted to be positioned at least partially within a bone and having a channeled portion and a ledge;

(b) a milling handle having a longitudinal axis, a shaft, and a notched receiver, wherein the shaft slides into and is received by the channeled portion of the milling body;

(c) a drill directing portion extending from the milling handle, wherein the drill directing portion comprises a drill receiving portion having an end and a cutting member receiving portion having an end, wherein the drill receiving portion has an axis parallel to the longitudinal axis of the milling handle, wherein the cutting member is located between the cutting member receiving portion end and the notched receiver, and wherein the drill receiving portion and the cutting member receiving portion remain connected at an angle to form an angled joint when the cutting member is not secured to the cutting member receiving portion end; and (d) a securing system configured to lock the milling body to the milling handle in at least one pre-determined position to prevent relative translation between the milling body and the milling handle and to hold the cutting member in a desired position relative to the ledge.

37. The in-line milling system of claim 36, wherein the securing system comprises a cross bar and indentation mechanism.

38. The in-line milling system of claim 37, wherein the cross bar and indentation mechanism comprises at least one indentation located on one of the milling handle and the milling body and a cross bar associated with the other of the milling handle and the milling body.

39. A method for preparing a bone for receiving an implant comprising:

(a) inserting a milling handle into a milling body adapted to be positioned at least partially within the bone;

(b) locking the milling handle and the milling body together to prevent relative translation between the milling handle and the milling body;

(c) securing a cutting member to the milling handle by sliding a locking member distally to fully engage a shank of the cutting member, wherein the milling handle comprises a drill receiving portion and a cutting member receiving portion that remain connected at an angle to form an angled joint when the cutting member is not secured to the milling handle;

(d) inserting the assembled milling system into the bone; and (e) activating a drill to rotate the cutting member to form a triangular-shaped cavity in the bone.

40. An in-line milling system for use with a cutting member comprising:

(a) a milling handle having a shaft with a longitudinal axis;

(b) a milling body adapted to be positioned at least partially within a bone and having a channeled portion and a conical portion, a distal end of the conical portion defining a ledge, the channeled portion and the conical portion adapted to receive the shaft of the milling handle; and (c) a securing system adapted to rigidly lock the milling handle to the milling body in at least one pre-determined position to prevent relative translation between the milling body and the milling handle, wherein the cutting member is associated with the milling handle and the at least one pre-determined position places the cutting member relative to the ledge and wherein the milling handle comprises a drill receiving portion and a cutting member receiving portion that remain connected at an angle to form an angled joint when the cutting member is not associated with the milling handle.

41. An in-line milling system for use with a cutting member comprising:

(a) a milling handle having a shaft with a longitudinal axis;

(b) a milling body adapted to be positioned at least partially within a bone, wherein the milling body comprises a channeled portion adapted to receive the milling handle such that the milling handle can translate within the milling body;

(c) a drill directing portion connected to the milling handle, the drill directing portion comprising a drill receiving portion and a cutting member receiving portion adapted to receive the cutting member, the drill receiving portion having an axis substantially parallel with the longitudinal axis of the milling handle and the cutting member receiving portion having an axis that is not parallel with the longitudinal axis of the milling handle, wherein the drill receiving portion and the cutting member receiving portion remain connected at an angle to form an angled joint when the cutting member is not secured to the cutting member receiving portion, and wherein the cutting member receiving portion is adapted to apply torque about a substantially straight axis shared by both the cutting member receiving portion and the cutting member in use; and (d) a securing system adapted to rigidly lock the milling handle to the milling body in at least one pre-determined position to prevent relative translation between the milling body and the milling handle.

42. A method for preparing a bone for receiving an implant comprising:
(a) inserting longitudinally a shaft of a milling handle into a channel portion of a milling body, the milling handle having a longitudinal axis;
(b) selecting from a plurality of pre-determined relative positions of the milling handle and the milling body the desired relative position of the milling handle and the milling body;
(c) locking the milling handle and the milling body in the desired pre-determined relative position;
(d) securing a cutting member to a cutting member receiving portion of the milling handle;
(e) connecting a drill to a drill receiving portion of the milling handle, the drill receiving portion having an axis substantially parallel to the longitudinal axis of the milling handle, wherein the drill receiving portion and the cutting member receiving portion remain connected at an angle to form an angled joint when the cutting member is not secured to the cutting member receiving portion;
(f) inserting the assembled milling system into the bone; and
(g) activating the drill to rotate the cutting member to form a triangular-shaped cavity in the bone.

* * * * *